(12) United States Patent
Porter et al.

(10) Patent No.: US 9,700,390 B2
(45) Date of Patent: Jul. 11, 2017

(54) SOFT-TISSUE PRESERVATION ARRANGEMENT AND METHOD

(71) Applicant: Biomet 3i LLC, Palm Beach Gardens, FL (US)

(72) Inventors: Stephan S. Porter, West Palm Beach, FL (US); Michael J. Traylor, Palm City, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 235 days.

(21) Appl. No.: 14/466,505

(22) Filed: Aug. 22, 2014

(65) Prior Publication Data

US 2016/0051344 A1 Feb. 25, 2016

(51) Int. Cl.
*A61C 8/00* (2006.01)

(52) U.S. Cl.
CPC .......... *A61C 8/008* (2013.01); *A61C 8/0001* (2013.01); *A61C 8/0036* (2013.01); *A61C 8/0077* (2013.01); *A61C 8/0098* (2013.01)

(58) Field of Classification Search
CPC ....... A61C 8/00; A61C 8/0004; A61C 8/0037; A61C 8/004; A61C 8/0054; A61C 8/0053; A61C 8/0077
USPC ................................................ 433/172–176
See application file for complete search history.

(56) References Cited

U.S. PATENT DOCUMENTS

| | | |
|---|---|---|
| RE27,227 E | 11/1971 | Harnsberger |
| 3,906,634 A | 9/1975 | Aspel |
| 3,919,772 A | 11/1975 | Lenczycki |
| 3,958,471 A | 5/1976 | Muller |
| 4,011,602 A | 3/1977 | Rybicki et al. |
| 4,056,585 A | 11/1977 | Waltke |
| 4,086,701 A | 5/1978 | Kawahara et al. |
| 4,177,562 A | 12/1979 | Miller et al. |
| 4,294,544 A | 10/1981 | Altschuler et al. |
| 4,306,862 A | 12/1981 | Knox |
| 4,325,373 A | 4/1982 | Slivenko et al. |

(Continued)

FOREIGN PATENT DOCUMENTS

| | | |
|---|---|---|
| DE | 10029256 | 11/2000 |
| KR | 1020140037719 A | 3/2014 |

(Continued)

OTHER PUBLICATIONS

Areva, Sam, et al., "Use of sol-gel-derived titania coating for direct soft tissue attachment", Wiley InterScience, pub. www.interscience.wiley.com, Jun. 2, 2004.

(Continued)

*Primary Examiner* — Alvin Stewart
(74) *Attorney, Agent, or Firm* — Schwegman Lundberg & Woessner, P.A.

(57) ABSTRACT

According to one aspect of the present invention, a soft tissue preservation arrangement includes a hollow shell defining an interior volume extending from a proximal opening to a distal opening. The proximal opening is defined by a first perimeter that is smaller than a second perimeter defining the distal opening such that the shell tapers outwardly from the first perimeter to the second perimeter. The second perimeter is asymmetrically scalloped. The hollow shell either (1) is transparent or semi-transparent or (2) has a color configured to correspond to a color of a gingival tissue or a tooth.

12 Claims, 8 Drawing Sheets

(56) References Cited

U.S. PATENT DOCUMENTS

| | | | |
|---|---|---|---|
| 4,341,312 A | 7/1982 | Scholer | |
| 4,364,381 A | 12/1982 | Sher et al. | |
| 4,439,152 A | 3/1984 | Small | |
| 4,543,953 A | 10/1985 | Slocum et al. | |
| 4,547,157 A | 10/1985 | Driskell | |
| 4,549,319 A * | 10/1985 | Meyer | A61C 8/0018 606/100 |
| 4,571,180 A | 2/1986 | Kulick | |
| 4,611,288 A | 9/1986 | Duret et al. | |
| 4,624,673 A | 11/1986 | Meyer | |
| 4,663,720 A | 5/1987 | Duret et al. | |
| 4,713,004 A | 12/1987 | Linkow et al. | |
| 4,756,689 A | 7/1988 | Lundgren | |
| 4,758,161 A | 7/1988 | Niznick | |
| 4,767,331 A | 8/1988 | Hoe | |
| 4,772,204 A | 9/1988 | Soderberg | |
| 4,821,200 A | 4/1989 | Öberg | |
| 4,842,518 A | 6/1989 | Linkow et al. | |
| 4,850,870 A | 7/1989 | Lazzara et al. | |
| 4,850,873 A | 7/1989 | Lazzara et al. | |
| 4,854,872 A | 8/1989 | Detsch | |
| 4,856,994 A | 8/1989 | Lazzara et al. | |
| 4,872,839 A | 10/1989 | Brajnovic | |
| 4,906,191 A | 3/1990 | Soderberg | |
| 4,906,420 A | 3/1990 | Brajnovic | |
| 4,931,016 A | 6/1990 | Sillard | |
| 4,935,635 A | 6/1990 | O'Harra | |
| 4,955,811 A | 9/1990 | Lazzara et al. | |
| 4,961,674 A | 10/1990 | Wang et al. | |
| 4,964,770 A | 10/1990 | Steinbichler et al. | |
| 4,986,753 A | 1/1991 | Sellers | |
| 4,988,297 A | 1/1991 | Lazzara et al. | |
| 4,988,298 A | 1/1991 | Lazzara et al. | |
| 4,998,881 A | 3/1991 | Lauks | |
| 5,000,685 A | 3/1991 | Brajnovic | |
| 5,006,069 A | 4/1991 | Lazzara et al. | |
| 5,015,183 A | 5/1991 | Fenick | |
| 5,015,186 A | 5/1991 | Detsch | |
| 5,030,096 A | 7/1991 | Hurson et al. | |
| 5,035,619 A | 7/1991 | Daftary | |
| 5,040,982 A | 8/1991 | Stefan-Dogar | |
| 5,040,983 A | 8/1991 | Binon | |
| 5,064,375 A | 11/1991 | Jörnéus | |
| 5,071,351 A | 12/1991 | Green, Jr. et al. | |
| 5,073,111 A | 12/1991 | Daftary | |
| 5,087,200 A | 2/1992 | Brajnovic et al. | |
| 5,100,323 A | 3/1992 | Friedman et al. | |
| 5,104,318 A | 4/1992 | Piche et al. | |
| 5,106,300 A | 4/1992 | Voitik | |
| 5,122,059 A | 6/1992 | Dürr et al. | |
| 5,125,839 A | 6/1992 | Ingber et al. | |
| 5,125,841 A | 6/1992 | Carlsson et al. | |
| 5,133,660 A | 7/1992 | Fenick | |
| 5,135,395 A | 8/1992 | Marlin | |
| 5,145,371 A | 9/1992 | Jörnéus | |
| 5,145,372 A | 9/1992 | Daftary et al. | |
| 5,176,516 A | 1/1993 | Koizumi | |
| 5,188,800 A | 2/1993 | Green, Jr. et al. | |
| 5,195,892 A | 3/1993 | Gersberg | |
| 5,205,745 A | 4/1993 | Kamiya et al. | |
| 5,209,659 A | 5/1993 | Friedman et al. | |
| 5,209,666 A | 5/1993 | Balfour et al. | |
| 5,213,502 A | 5/1993 | Daftary | |
| 5,221,204 A | 6/1993 | Kruger et al. | |
| 5,237,998 A | 8/1993 | Duret et al. | |
| 5,246,370 A | 9/1993 | Coatoam | |
| 5,257,184 A | 10/1993 | Mushabac | |
| 5,281,140 A | 1/1994 | Niznick | |
| 5,286,195 A | 2/1994 | Clostermann | |
| 5,286,196 A | 2/1994 | Brajnovic et al. | |
| 5,292,252 A | 3/1994 | Nickerson et al. | |
| 5,297,963 A | 3/1994 | Dafatry | |
| 5,302,125 A | 4/1994 | Kownacki et al. | |
| 5,312,254 A | 5/1994 | Rosenlicht | |
| 5,312,409 A | 5/1994 | McLaughlin et al. | |
| 5,316,476 A | 5/1994 | Krauser | |
| 5,320,529 A | 6/1994 | Pompa | |
| 5,328,371 A | 7/1994 | Hund et al. | |
| 5,334,024 A | 8/1994 | Niznick | |
| 5,336,090 A | 8/1994 | Wilson, Jr. et al. | |
| 5,338,196 A | 8/1994 | Beaty et al. | |
| 5,338,198 A | 8/1994 | Wu et al. | |
| 5,343,391 A | 8/1994 | Mushabac | |
| 5,344,457 A | 9/1994 | Pilliar et al. | |
| 5,350,297 A | 9/1994 | Cohen | |
| 5,359,511 A | 10/1994 | Schroeder et al. | |
| 5,362,234 A | 11/1994 | Salazar et al. | |
| 5,362,235 A | 11/1994 | Daftary | |
| 5,368,483 A | 11/1994 | Sutter et al. | |
| 5,370,692 A | 12/1994 | Fink et al. | |
| 5,372,502 A | 12/1994 | Massen et al. | |
| 5,386,292 A | 1/1995 | Massen et al. | |
| 5,413,481 A | 5/1995 | Göppel et al. | |
| 5,417,568 A | 5/1995 | Giglio | |
| 5,417,569 A | 5/1995 | Perisse | |
| 5,417,570 A | 5/1995 | Zuest et al. | |
| 5,419,702 A | 5/1995 | Beaty et al. | |
| 5,431,567 A | 7/1995 | Datary | |
| 5,433,606 A | 7/1995 | Niznick et al. | |
| 5,437,551 A | 8/1995 | Chalifoux | |
| 5,440,393 A | 8/1995 | Wenz | |
| 5,452,219 A | 9/1995 | Dehoff et al. | |
| 5,458,488 A | 10/1995 | Chalifoux | |
| 5,476,382 A | 12/1995 | Daftary | |
| 5,476,383 A | 12/1995 | Beaty et al. | |
| 5,492,471 A | 2/1996 | Singer | |
| 5,516,288 A | 5/1996 | Sichler et al. | |
| 5,527,182 A | 6/1996 | Willoughby | |
| 5,533,898 A | 7/1996 | Mena | |
| 5,538,426 A | 7/1996 | Harding et al. | |
| 5,547,377 A | 8/1996 | Daftary | |
| 5,556,278 A | 9/1996 | Meitner | |
| 5,564,921 A | 10/1996 | Marlin | |
| 5,564,924 A | 10/1996 | Kwan | |
| 5,569,578 A | 10/1996 | Mushabac | |
| 5,571,016 A | 11/1996 | Ingber et al. | |
| 5,575,656 A | 11/1996 | Hajjar | |
| 5,580,244 A | 12/1996 | White | |
| 5,580,246 A | 12/1996 | Fried | |
| 5,595,703 A | 1/1997 | Swaelens et al. | |
| 5,599,185 A | 2/1997 | Greenberg | |
| 5,613,832 A | 3/1997 | Su | |
| 5,613,852 A | 3/1997 | Bavitz | |
| 5,630,717 A | 5/1997 | Zuest | |
| 5,636,986 A | 6/1997 | Prezeshkian | |
| 5,651,675 A | 7/1997 | Singer | |
| 5,652,709 A | 7/1997 | Andersson et al. | |
| 5,658,147 A | 8/1997 | Phimmasone | |
| 5,662,476 A | 9/1997 | Ingber et al. | |
| 5,674,069 A | 10/1997 | Osorio | |
| 5,674,071 A | 10/1997 | Beaty et al. | |
| 5,674,073 A | 10/1997 | Ingber et al. | |
| 5,681,167 A | 10/1997 | Lazarof | |
| 5,685,714 A | 11/1997 | Beaty | |
| 5,685,715 A | 11/1997 | Beaty et al. | |
| 5,688,283 A | 11/1997 | Knapp | |
| 5,704,936 A | 1/1998 | Mazel | |
| 5,718,579 A | 2/1998 | Kennedy | |
| 5,725,376 A | 3/1998 | Poirier | |
| 5,733,124 A | 3/1998 | Kwan | |
| 5,741,215 A | 4/1998 | D'Urso | |
| 5,743,916 A | 4/1998 | Greenberg | |
| 5,759,036 A | 6/1998 | Hinds | |
| 5,762,125 A | 6/1998 | Mastrorio | |
| 5,762,500 A | 6/1998 | Lazarof | |
| 5,768,134 A | 6/1998 | Swaelens et al. | |
| 5,769,636 A | 6/1998 | Di Sario | |
| 5,779,480 A | 7/1998 | Groll et al. | |
| 5,779,481 A | 7/1998 | Aires | |
| 5,791,902 A | 8/1998 | Lauks | |
| 5,800,168 A | 9/1998 | Cascione et al. | |
| 5,810,589 A | 9/1998 | Michnick et al. | |
| 5,810,592 A * | 9/1998 | Daftary | A61C 8/005 433/172 |

(56) References Cited

U.S. PATENT DOCUMENTS

| | | |
|---|---|---|
| 5,813,858 A | 9/1998 | Singer |
| 5,823,778 A | 10/1998 | Schmitt et al. |
| 5,842,859 A | 12/1998 | Palacci |
| 5,846,079 A | 12/1998 | Knode |
| 5,851,115 A | 12/1998 | Carlsson et al. |
| 5,857,853 A | 1/1999 | Van Nifterick et al. |
| 5,871,358 A | 2/1999 | Ingber et al. |
| 5,873,722 A | 2/1999 | Lazzara et al. |
| 5,876,204 A | 3/1999 | Day et al. |
| 5,885,078 A | 3/1999 | Cagna et al. |
| 5,888,034 A | 3/1999 | Greenberg |
| 5,890,902 A | 4/1999 | Sapian |
| 5,899,695 A | 5/1999 | Lazzara et al. |
| 5,899,697 A | 5/1999 | Lazzara et al. |
| 5,904,483 A | 5/1999 | Wade |
| 5,915,962 A | 6/1999 | Rosenlicht |
| 5,927,982 A | 7/1999 | Kruger |
| 5,931,675 A | 8/1999 | Callan |
| 5,938,443 A | 8/1999 | Lazzara et al. |
| 5,947,732 A | 9/1999 | Beaty et al. |
| 5,954,769 A | 9/1999 | Rosenlicht |
| 5,964,591 A | 10/1999 | Beaty et al. |
| 5,967,777 A | 10/1999 | Klein et al. |
| 5,984,681 A | 11/1999 | Huang |
| 5,989,025 A | 11/1999 | Conley |
| 5,989,026 A | 11/1999 | Rogers et al. |
| 5,989,028 A | 11/1999 | Niznick |
| 5,989,029 A | 11/1999 | Osorio |
| 5,989,258 A | 11/1999 | Hattori |
| 5,997,681 A | 12/1999 | Kinzie |
| 6,000,939 A | 12/1999 | Ray et al. |
| 6,008,905 A | 12/1999 | Breton et al. |
| 6,024,567 A | 2/2000 | Callan |
| 6,030,219 A | 2/2000 | Zuest et al. |
| 6,068,479 A | 5/2000 | Kwan |
| 6,099,311 A | 8/2000 | Wagner et al. |
| 6,099,313 A | 8/2000 | Dorken et al. |
| 6,099,314 A | 8/2000 | Kopelman et al. |
| 6,120,293 A | 9/2000 | Lazzara et al. |
| 6,129,548 A | 10/2000 | Lazzara et al. |
| 6,135,773 A | 10/2000 | Lazzara |
| 6,142,782 A | 11/2000 | Lazarof |
| 6,152,737 A | 11/2000 | Beaty et al. |
| 6,164,969 A | 12/2000 | Dinkelacker |
| 6,168,435 B1 | 1/2001 | Beaty et al. |
| 6,174,168 B1 | 1/2001 | Dehoff et al. |
| 6,175,413 B1 | 1/2001 | Lucas |
| 6,190,169 B1 | 2/2001 | Bluemli et al. |
| 6,197,410 B1 | 3/2001 | Vallittu et al. |
| 6,200,125 B1 | 3/2001 | Akutagawa |
| 6,206,693 B1 | 3/2001 | Hultgren |
| 6,210,162 B1 | 4/2001 | Chishti |
| 6,217,334 B1 | 4/2001 | Hultgren |
| 6,227,857 B1 | 5/2001 | Morgan et al. |
| 6,227,859 B1 | 5/2001 | Sutter |
| 6,283,753 B1 | 9/2001 | Willoughby |
| 6,287,117 B1 | 9/2001 | Niznick |
| 6,287,119 B1 | 9/2001 | van Nifterick |
| 6,296,483 B1 | 10/2001 | Champleboux |
| 6,305,939 B1 | 10/2001 | Dawood |
| 6,312,259 B1 | 11/2001 | Kvarnstrom et al. |
| 6,319,000 B1 | 11/2001 | Branemark |
| 6,322,728 B1 | 11/2001 | Brodkin |
| 6,343,930 B1 | 2/2002 | Beaty et al. |
| 6,382,975 B1 | 5/2002 | Poirier |
| 6,402,707 B1 | 6/2002 | Ernst |
| 6,419,491 B1 | 7/2002 | Ricci et al. |
| 6,426,114 B1 | 7/2002 | Troczynski et al. |
| 6,428,803 B1 | 8/2002 | Ewers et al. |
| 6,431,866 B2 | 8/2002 | Hurson |
| 6,431,867 B1 | 8/2002 | Gittelson et al. |
| 6,482,444 B1 | 11/2002 | Bellantone et al. |
| 6,488,503 B1 | 12/2002 | Lichkus et al. |
| 6,497,573 B2 | 12/2002 | Wagner et al. |
| 6,497,574 B1 | 12/2002 | Miller |
| 6,537,069 B1* | 3/2003 | Simmons, Jr. ......... A61C 8/001 433/173 |
| 6,540,784 B2 | 4/2003 | Barlow |
| 6,558,162 B1 | 5/2003 | Porter et al. |
| 6,568,936 B2 | 5/2003 | MacDougald |
| 6,575,751 B1 | 6/2003 | Lehmann et al. |
| 6,594,539 B1 | 7/2003 | Geng |
| 6,610,079 B1 | 8/2003 | Li |
| 6,619,958 B2 | 9/2003 | Beaty et al. |
| 6,629,840 B2 | 10/2003 | Chishti |
| 6,634,883 B2 | 10/2003 | Ranalli |
| 6,644,970 B1 | 11/2003 | Lin |
| 6,648,640 B2 | 11/2003 | Rubbert et al. |
| 6,663,388 B1 | 12/2003 | Schar et al. |
| 6,671,539 B2 | 12/2003 | Gateno et al. |
| 6,672,870 B2 | 1/2004 | Knapp |
| D486,914 S | 2/2004 | Schulter et al. |
| 6,688,887 B2 | 2/2004 | Morgan |
| 6,691,764 B2 | 2/2004 | Embert |
| 6,733,291 B1* | 5/2004 | Hurson ............... A61C 8/0054 433/173 |
| 6,743,491 B2 | 6/2004 | Cirincione et al. |
| 6,755,652 B2 | 6/2004 | Nanni |
| D493,535 S | 7/2004 | Whitehead |
| 6,772,026 B2 | 8/2004 | Bradbury |
| 6,776,614 B2 | 8/2004 | Wiechmann et al. |
| 6,783,359 B2 | 8/2004 | Kapit |
| 6,790,040 B2 | 9/2004 | Amber et al. |
| 6,793,491 B2 | 9/2004 | Klein et al. |
| 6,808,659 B2 | 10/2004 | Schulman |
| 6,814,575 B2 | 11/2004 | Poirier |
| 6,821,462 B2 | 11/2004 | Schulman et al. |
| 6,829,498 B2 | 12/2004 | Kipke et al. |
| D503,804 S | 4/2005 | Phleps et al. |
| 6,882,894 B2 | 4/2005 | Durbin et al. |
| 6,885,464 B1 | 4/2005 | Pfeiffer et al. |
| 6,902,401 B2 | 6/2005 | Jorneus et al. |
| D507,052 S | 7/2005 | Wohrle |
| 6,913,463 B2 | 7/2005 | Blacklock |
| 6,926,442 B2 | 8/2005 | Stöckl |
| 6,926,525 B1 | 8/2005 | Ronvig |
| 6,939,489 B2 | 9/2005 | Moszner et al. |
| 6,942,699 B2 | 9/2005 | Stone et al. |
| 6,953,383 B2 | 10/2005 | Rothenberger |
| 6,957,118 B2 | 10/2005 | Kopelman et al. |
| D511,833 S | 11/2005 | Wohrle |
| 6,966,772 B2 | 11/2005 | Malin et al. |
| 6,970,760 B2 | 11/2005 | Wolf et al. |
| 6,971,877 B2 | 12/2005 | Harter |
| 6,984,392 B2 | 1/2006 | Bechert et al. |
| 6,994,549 B2 | 2/2006 | Brodkin et al. |
| 7,010,150 B1 | 3/2006 | Pfeiffer et al. |
| 7,010,153 B2 | 3/2006 | Zimmermann |
| 7,012,988 B2 | 3/2006 | Adler et al. |
| 7,018,207 B2 | 3/2006 | Prestipino |
| 7,021,934 B2 | 4/2006 | Aravena |
| 7,029,275 B2 | 4/2006 | Rubbert et al. |
| 7,044,735 B2 | 5/2006 | Malin |
| 7,056,115 B2 | 6/2006 | Phan et al. |
| 7,056,117 B2 | 6/2006 | Simmons, Jr. |
| 7,056,472 B1 | 6/2006 | Behringer |
| 7,059,856 B2 | 6/2006 | Marotta |
| 7,066,736 B2 | 6/2006 | Kumar et al. |
| 7,067,169 B2 | 6/2006 | Liu et al. |
| 7,084,868 B2 | 8/2006 | Farag et al. |
| 7,086,860 B2 | 8/2006 | Schuman et al. |
| 7,097,451 B2 | 8/2006 | Tang |
| 7,104,795 B2 | 9/2006 | Dadi |
| 7,110,844 B2 | 9/2006 | Kopelman |
| 7,112,065 B2 | 9/2006 | Kopelman |
| 7,118,375 B2 | 10/2006 | Durbin et al. |
| D532,991 S | 12/2006 | Gozzi |
| 7,153,132 B2 | 12/2006 | Tedesco |
| 7,153,135 B1 | 12/2006 | Thomas |
| 7,163,443 B2 | 1/2007 | Basler et al. |
| 7,175,434 B2 | 2/2007 | Brajnovic |
| 7,175,435 B2 | 2/2007 | Andersson et al. |
| 7,178,731 B2 | 2/2007 | Basler |
| 7,214,062 B2 | 5/2007 | Morgan |

(56) References Cited

U.S. PATENT DOCUMENTS

| | | | |
|---|---|---|---|
| 7,220,124 B2 | 5/2007 | Taub et al. |
| 7,228,191 B2 | 6/2007 | Hofmeister et al. |
| 7,236,842 B2 | 6/2007 | Kopelman et al. |
| 7,281,927 B2 | 10/2007 | Marotta |
| 7,286,954 B2 | 10/2007 | Kopelman et al. |
| 7,303,420 B2 | 12/2007 | Huch et al. |
| 7,319,529 B2 | 1/2008 | Babayoff |
| 7,322,746 B2 | 1/2008 | Beckhaus et al. |
| 7,322,824 B2 | 1/2008 | Schmitt |
| 7,324,680 B2 | 1/2008 | Zimmermann |
| 7,329,122 B1 | 2/2008 | Scott |
| 7,333,874 B2 | 2/2008 | Taub et al. |
| 7,335,876 B2 | 2/2008 | Eiff et al. |
| D565,184 S | 3/2008 | Royzen |
| 7,338,286 B2 | 3/2008 | Porter et al. |
| 7,341,756 B2 | 3/2008 | Liu et al. |
| 7,367,801 B2 | 5/2008 | Saliger |
| 7,379,584 B2 | 5/2008 | Rubbert et al. |
| D571,471 S | 6/2008 | Stöckl |
| 7,381,191 B2 | 6/2008 | Fallah |
| 7,383,094 B2 | 6/2008 | Kopelman et al. |
| D575,747 S | 8/2008 | Abramovich et al. |
| 7,421,608 B2 | 9/2008 | Schron |
| 7,425,131 B2 | 9/2008 | Amber et al. |
| 7,429,175 B2 | 9/2008 | Gittelson |
| 7,435,088 B2 | 10/2008 | Brajnovic |
| 7,476,100 B2 | 1/2009 | Kuo |
| 7,481,647 B2 | 1/2009 | Sambu et al. |
| 7,484,959 B2 | 2/2009 | Porter et al. |
| 7,488,174 B2 | 2/2009 | Kopelman et al. |
| 7,491,058 B2 | 2/2009 | Jorneus et al. |
| 7,497,619 B2 | 3/2009 | Stoeckl |
| 7,497,983 B2 | 3/2009 | Khan et al. |
| 7,520,747 B2 | 4/2009 | Stonisch |
| 7,522,764 B2 | 4/2009 | Schwotzer |
| 7,534,266 B2 | 5/2009 | Kluger |
| 7,536,234 B2 | 5/2009 | Kopelman et al. |
| 7,545,372 B2 | 6/2009 | Kopelman et al. |
| 7,551,760 B2 | 6/2009 | Scharlack et al. |
| 7,555,403 B2 | 6/2009 | Kopelman et al. |
| 7,556,496 B2 | 7/2009 | Cinader, Jr. et al. |
| 7,559,692 B2 | 7/2009 | Beckhaus et al. |
| 7,563,397 B2 | 7/2009 | Schulman et al. |
| D597,769 S | 8/2009 | Richter et al. |
| 7,572,058 B2 | 8/2009 | Pruss et al. |
| 7,572,125 B2 | 8/2009 | Brajnovic |
| 7,574,025 B2 | 8/2009 | Feldman |
| 7,578,673 B2 | 8/2009 | Wen et al. |
| 7,580,502 B2 | 8/2009 | Dalpiaz et al. |
| 7,581,951 B2 | 9/2009 | Lehmann et al. |
| 7,582,855 B2 | 9/2009 | Pfeiffer |
| 7,628,537 B2 | 12/2009 | Schulze-Ganzlin |
| 7,632,097 B2 | 12/2009 | Clerck |
| 7,653,455 B2 | 1/2010 | Cnader, Jr. et al. |
| 7,654,823 B2 | 2/2010 | Dadi |
| 7,655,586 B1 | 2/2010 | Brodkin et al. |
| 7,658,610 B2 | 2/2010 | Knopp |
| 7,661,956 B2 | 2/2010 | Powell et al. |
| 7,665,989 B2 | 2/2010 | Brajnovic et al. |
| 7,679,723 B2 | 3/2010 | Schwotzer |
| 7,687,754 B2 | 3/2010 | Eiff et al. |
| 7,689,308 B2 | 3/2010 | Holzner et al. |
| D614,210 S | 4/2010 | Basler et al. |
| 7,698,014 B2 | 4/2010 | Dunne et al. |
| 7,758,346 B1 | 7/2010 | Letcher |
| 7,774,084 B2 | 8/2010 | Cinader, Jr. |
| 7,780,446 B2 | 8/2010 | Sanchez et al. |
| 7,780,907 B2 | 8/2010 | Schmidt et al. |
| 7,785,007 B2 | 8/2010 | Stoeckl |
| 7,787,132 B2 | 8/2010 | Körner et al. |
| 7,796,811 B2 | 9/2010 | Orth et al. |
| 7,798,708 B2 | 9/2010 | Erhardt et al. |
| 7,801,632 B2 | 9/2010 | Orth et al. |
| 7,815,371 B2 | 10/2010 | Schulze-Ganzlin |
| 7,824,181 B2 | 11/2010 | Sers |
| D629,908 S | 12/2010 | Jerger et al. |
| 7,855,354 B2 | 12/2010 | Eiff |
| 7,865,261 B2 | 1/2011 | Pfeiffer |
| 7,876,877 B2 | 1/2011 | Stockl |
| 7,901,209 B2 | 3/2011 | Saliger et al. |
| 7,906,132 B2 | 3/2011 | Ziegler et al. |
| 7,982,731 B2 | 7/2011 | Orth et al. |
| 7,985,119 B2 | 7/2011 | Basler et al. |
| 7,986,415 B2 | 7/2011 | Thiel et al. |
| 7,988,449 B2 | 8/2011 | Amber et al. |
| 8,011,925 B2 | 9/2011 | Powell et al. |
| 8,011,927 B2 | 9/2011 | Merckmans, III et al. |
| 8,026,943 B2 | 9/2011 | Weber et al. |
| 8,033,826 B2 | 10/2011 | Towse et al. |
| 8,038,440 B2 | 10/2011 | Swaelens et al. |
| 8,043,091 B2 | 10/2011 | Schmitt |
| 8,047,895 B2 | 11/2011 | Basler |
| 8,057,912 B2 | 11/2011 | Basler et al. |
| 8,062,034 B2 | 11/2011 | Hanisch et al. |
| 8,075,313 B2 | 12/2011 | Ranck et al. |
| 8,083,522 B2 | 12/2011 | Karkar et al. |
| 8,105,081 B2 | 1/2012 | Bavar |
| 8,185,224 B2 | 5/2012 | Powell et al. |
| 8,226,654 B2 | 7/2012 | Ranck et al. |
| 8,257,083 B2 | 9/2012 | Berckmans, III et al. |
| 8,272,870 B2 | 9/2012 | Van Lierde et al. |
| 8,309,162 B2 | 11/2012 | Charlton et al. |
| 8,425,231 B1 * | 4/2013 | Hochman ............ A61C 8/008 |
| | | 433/173 |
| 9,089,382 B2 * | 7/2015 | Hochman ............ A61C 8/0001 |
| 2001/0008751 A1 | 7/2001 | Chishti et al. |
| 2001/0034010 A1 | 10/2001 | MacDougald et al. |
| 2002/0010568 A1 | 1/2002 | Rubbert et al. |
| 2002/0028418 A1 | 3/2002 | Farag et al. |
| 2002/0039717 A1 | 4/2002 | Amber et al. |
| 2002/0160337 A1 | 10/2002 | Klein et al. |
| 2002/0167100 A1 | 11/2002 | Moszner |
| 2003/0130605 A1 | 7/2003 | Besek |
| 2003/0222366 A1 | 12/2003 | Stangel |
| 2004/0029074 A1 | 2/2004 | Brajnovic |
| 2004/0048227 A1 | 3/2004 | Brajnovic |
| 2004/0121286 A1 * | 6/2004 | Aravena ............ A61C 8/0006 |
| | | 433/173 |
| 2004/0132603 A1 | 7/2004 | Narhi et al. |
| 2004/0180308 A1 | 9/2004 | Ebi et al. |
| 2004/0219477 A1 | 11/2004 | Harter |
| 2004/0219479 A1 | 11/2004 | Malin et al. |
| 2004/0219490 A1 | 11/2004 | Gartner et al. |
| 2004/0220691 A1 | 11/2004 | Hofmeister et al. |
| 2004/0241611 A1 | 12/2004 | Amber et al. |
| 2004/0243481 A1 | 12/2004 | Bradbury et al. |
| 2004/0259051 A1 | 12/2004 | Brajnovic |
| 2005/0023710 A1 | 2/2005 | Brodkin et al. |
| 2005/0056350 A1 | 3/2005 | Dolabdjian et al. |
| 2005/0070782 A1 | 3/2005 | Brodkin |
| 2005/0084144 A1 | 4/2005 | Feldman |
| 2005/0100861 A1 | 5/2005 | Choi et al. |
| 2005/0170311 A1 | 8/2005 | Tardieu et al. |
| 2005/0271996 A1 | 12/2005 | Sporbert et al. |
| 2005/0277089 A1 | 12/2005 | Brajnovic |
| 2005/0277090 A1 | 12/2005 | Anderson et al. |
| 2005/0277091 A1 | 12/2005 | Andersson et al. |
| 2005/0282106 A1 | 12/2005 | Sussman et al. |
| 2005/0283065 A1 | 12/2005 | Babayoff |
| 2006/0006561 A1 | 1/2006 | Brajnovic |
| 2006/0008763 A1 | 1/2006 | Brajnovic |
| 2006/0008770 A1 | 1/2006 | Brajnovic et al. |
| 2006/0046229 A1 | 3/2006 | Teich |
| 2006/0093988 A1 | 5/2006 | Swaelens et al. |
| 2006/0094951 A1 | 5/2006 | Dean et al. |
| 2006/0127848 A1 | 6/2006 | Sogo et al. |
| 2006/0210949 A1 | 9/2006 | Stoop |
| 2006/0252009 A1 | 11/2006 | Gogarnoiu |
| 2006/0263741 A1 | 11/2006 | Imgrund et al. |
| 2006/0281041 A1 | 12/2006 | Rubbert et al. |
| 2007/0015111 A1 | 1/2007 | Kopelman et al. |
| 2007/0031790 A1 | 2/2007 | Raby et al. |
| 2007/0065777 A1 | 3/2007 | Becker |
| 2007/0077532 A1 | 4/2007 | Harter |

(56) References Cited

U.S. PATENT DOCUMENTS

| | | |
|---|---|---|
| 2007/0092854 A1 | 4/2007 | Powell et al. |
| 2007/0141525 A1 | 6/2007 | Cinader, Jr. |
| 2007/0211081 A1 | 9/2007 | Quadling et al. |
| 2007/0218426 A1 | 9/2007 | Quadling et al. |
| 2007/0264612 A1 | 11/2007 | Mount |
| 2007/0269769 A1 | 11/2007 | Marchesi |
| 2007/0281277 A1 | 12/2007 | Brajnovic |
| 2008/0038692 A1 | 2/2008 | Andersson et al. |
| 2008/0044794 A1 | 2/2008 | Brajnovic |
| 2008/0057467 A1 | 3/2008 | Gittelson |
| 2008/0070181 A1 | 3/2008 | Abolfathi et al. |
| 2008/0085489 A1 | 4/2008 | Schmitt |
| 2008/0090210 A1 | 4/2008 | Brajnovic |
| 2008/0114371 A1 | 5/2008 | Kluger |
| 2008/0118895 A1 | 5/2008 | Brajnovic |
| 2008/0124676 A1 | 5/2008 | Marotta |
| 2008/0153060 A1 | 6/2008 | De Moyer |
| 2008/0153061 A1 | 6/2008 | Marcello |
| 2008/0153065 A1 | 6/2008 | Brajnovic et al. |
| 2008/0153069 A1 | 6/2008 | Holzner et al. |
| 2008/0176189 A1 | 7/2008 | Stonisch |
| 2008/0206714 A1 | 8/2008 | Schmitt |
| 2008/0233537 A1 | 9/2008 | Amber et al. |
| 2008/0233539 A1 | 9/2008 | Rossler et al. |
| 2008/0241798 A1 | 10/2008 | Holzner et al. |
| 2008/0261165 A1 | 10/2008 | Steingart et al. |
| 2008/0261176 A1 | 10/2008 | Hurson |
| 2008/0286722 A1 | 11/2008 | Berckmans, III et al. |
| 2008/0300716 A1 | 12/2008 | Kopelman et al. |
| 2009/0017418 A1 | 1/2009 | Gittelson |
| 2009/0026643 A1 | 1/2009 | Wiest et al. |
| 2009/0042167 A1 | 2/2009 | Van Der Zel |
| 2009/0081616 A1 | 3/2009 | Pfeiffer |
| 2009/0087817 A1 | 4/2009 | Jansen et al. |
| 2009/0092948 A1 | 4/2009 | Gantes |
| 2009/0098510 A1 | 4/2009 | Zhang |
| 2009/0098511 A1 | 4/2009 | Zhang |
| 2009/0123045 A1 | 5/2009 | Quadling et al. |
| 2009/0123887 A1 | 5/2009 | Brajnovic |
| 2009/0130629 A1 | 5/2009 | Towse et al. |
| 2009/0130630 A1 | 5/2009 | Suttin et al. |
| 2009/0186319 A1 | 7/2009 | Sager |
| 2009/0187393 A1 | 7/2009 | Van Lierde et al. |
| 2009/0220134 A1 | 9/2009 | Cahill et al. |
| 2009/0220916 A1 | 9/2009 | Fisker et al. |
| 2009/0220917 A1 | 9/2009 | Jensen |
| 2009/0239195 A1 | 9/2009 | Wohrle et al. |
| 2009/0239197 A1 | 9/2009 | Brajnovic |
| 2009/0239200 A1 | 9/2009 | Brajnovic et al. |
| 2009/0253097 A1 | 10/2009 | Brajnovic |
| 2009/0263764 A1 | 10/2009 | Berckmans, III et al. |
| 2009/0287332 A1 | 11/2009 | Adusumilli et al. |
| 2009/0298009 A1 | 12/2009 | Brajnovic |
| 2009/0298017 A1 | 12/2009 | Boerjes et al. |
| 2009/0317763 A1 | 12/2009 | Brajnovic |
| 2009/0325122 A1 | 12/2009 | Brajnovic et al. |
| 2010/0009314 A1 | 1/2010 | Tardieu et al. |
| 2010/0028827 A1 | 2/2010 | Andersson et al. |
| 2010/0038807 A1 | 2/2010 | Brodkin et al. |
| 2010/0075275 A1 | 3/2010 | Brajnovic |
| 2010/0092904 A1 | 4/2010 | Esposti et al. |
| 2010/0105008 A1 | 4/2010 | Powell et al. |
| 2010/0151420 A1 | 6/2010 | Ranck |
| 2010/0151423 A1 | 6/2010 | Ranck et al. |
| 2010/0173260 A1 | 7/2010 | Sogo et al. |
| 2010/0209877 A1 | 8/2010 | Hogan et al. |
| 2010/0280798 A1 | 11/2010 | Pattijn et al. |
| 2010/0330533 A1 | 12/2010 | Cottrell |
| 2011/0008751 A1 | 1/2011 | Pettersson |
| 2011/0027339 A1 | 2/2011 | Mao |
| 2011/0060558 A1 | 3/2011 | Pettersson |
| 2011/0123959 A1 | 5/2011 | Sicurelli et al. |
| 2011/0129792 A1 | 6/2011 | Berckmans, III et al. |
| 2011/0129797 A1* | 6/2011 | Neumeyer ........... A61C 8/0001 433/173 |
| 2011/0159455 A1 | 6/2011 | Stumpel |
| 2011/0183289 A1 | 7/2011 | Powell et al. |
| 2011/0191081 A1 | 8/2011 | Malfliet et al. |
| 2011/0200967 A1 | 8/2011 | Laizure, Jr. |
| 2011/0244426 A1 | 10/2011 | Amber et al. |
| 2011/0269104 A1 | 11/2011 | Berckmans, III et al. |
| 2011/0275032 A1 | 11/2011 | Tardieu et al. |
| 2011/0306008 A1 | 12/2011 | Suttin et al. |
| 2011/0306009 A1 | 12/2011 | Suttin et al. |
| 2011/0306014 A1 | 12/2011 | Conte et al. |
| 2012/0010740 A1 | 1/2012 | Swaelens et al. |
| 2012/0135370 A1 | 5/2012 | Ranck et al. |
| 2012/0164593 A1 | 6/2012 | Bavar |
| 2012/0164893 A1 | 6/2012 | Misuzuka et al. |
| 2012/0214130 A1 | 8/2012 | Krivoruk |
| 2012/0282573 A1 | 11/2012 | Mao |
| 2012/0295223 A1* | 11/2012 | Robb ................. A61C 8/008 433/173 |
| 2012/0330315 A1 | 12/2012 | Ranck et al. |
| 2013/0101964 A1* | 4/2013 | Fudim ............... A61C 8/0001 433/214 |
| 2013/0177872 A1* | 7/2013 | Blaisdell ............ A61C 8/008 433/173 |
| 2013/0189646 A1* | 7/2013 | Hochman ........... A61C 8/0001 433/174 |
| 2013/0288202 A1* | 10/2013 | Hochman ........... A61C 8/008 433/175 |
| 2014/0205969 A1* | 7/2014 | Marlin .............. A61C 8/0001 433/173 |
| 2014/0319713 A1* | 10/2014 | Blaisdell ............ A61C 13/34 264/19 |
| 2015/0004563 A1* | 1/2015 | Blaisdell ............ A61C 13/34 433/173 |
| 2015/0044635 A1* | 2/2015 | Wang ............... A61C 8/005 433/173 |
| 2015/0289952 A1* | 10/2015 | Hochman ........... A61C 8/0001 433/173 |
| 2016/0051344 A1* | 2/2016 | Porter ............... A61C 8/0001 433/175 |
| 2016/0074141 A1* | 3/2016 | Lozada .............. A61C 8/0089 433/75 |

FOREIGN PATENT DOCUMENTS

| | | |
|---|---|---|
| WO | WO 94/26200 | 11/1994 |
| WO | WO 99/32045 | 7/1999 |
| WO | WO 00/08415 | 2/2000 |
| WO | WO 01/58379 | 8/2001 |
| WO | WO 02/053055 | 7/2002 |
| WO | WO 03/024352 | 3/2003 |
| WO | WO 2004/030565 | 4/2004 |
| WO | WO 2004/037110 | 5/2004 |
| WO | WO 2004/075771 | 9/2004 |
| WO | WO 2004/087000 | 10/2004 |
| WO | WO 2004/098435 | 11/2004 |
| WO | WO 2006/014130 | 2/2006 |
| WO | WO 2006/062459 | 6/2006 |
| WO | WO 2006/082198 | 8/2006 |
| WO | WO 2007/005490 | 1/2007 |
| WO | WO 2007/033157 | 3/2007 |
| WO | WO 2007/104842 | 9/2007 |
| WO | WO 2007/129955 | 11/2007 |
| WO | WO 2008/057955 | 5/2008 |
| WO | WO 2008/083857 | 7/2008 |
| WO | WO 2009/146164 | 12/2009 |

OTHER PUBLICATIONS

Biomet 3i—Manual entitled "Navigator™ System for CT Guided Surgery Manual", Revision A Oct. 2007—34 pages.

Biomet 3i et al., ART1011A NanoTite Implant System Brochure, "NanoTitle Prevail Implants: Crestal Bone Preservation in the Aesthetic Zone", vol. 6, Issue 2, Jul. 2007.

Biomet 3i et al., ART1060 EncodeCP Brochure, "Provisionalization with Soft Tissue Sculpting Prior to Fabrication of a CAD/CAM Abutment", vol. 7, Issue 3, Jun. 2009.

(56) References Cited

OTHER PUBLICATIONS

Biomet 3i et al., PreFormance Temporary Cylinder Brochure, "Immediate Provisional Restoration of Implants with PreFormance Provisional Components", May 2007.

Biomet 3i, ART1018 Provisional Components Brochure, "Your Patients Require Immediate Aesthetic Solutions . . . Biomet 3i Has Optimal Products", Jun. 2009.

Biomet 3i, ART953C PreFormance Brochure,"Rapid Adjustment. Enduring Strength. Aesthetic Design.", Feb. 2008.

Biomet 3i, Osseotite Implants, Restorative Manual, Dec. 2009.

Francois Goulette, "A New Method and a Clinical case for Computer Assisted Dental Implantology." Retrieved from Summer European university in surgical Robotics, URL:www.lirmm.fr/manifs/UEE/docs/students/goulette.pdf, Sep. 6, 2003 (7 pages).

Frojd, Victoria, et al., "Effect of Nanoporous TiO2 Coating and Anodized Ca2 Modification of Titanium Surfaces on Early Microbial Biofilm Formation", BMC Oral Health, 2011.

Giordano, Russell, II, Compendium, Clinical Materials Review, "Zirconia: A Proven, Durable Ceramic for Esthetic Restorations", vol. 33, No. 1, Jan. 2012.

Jakob Brief, "Accuracy of image-guided implantology." Retrieved from Google, <URL:sitemaker.umich.edu/sarmentlab/files/robodent_vs_denx_coir_05.pdf, Aug. 20, 2004 (7 pages).

Kan, J, Y.K. et al., "Interimplant Papilla Preserv. in the Esthetic Zone: A Report of Six Consecutive Cases", The Int'l Jrnl of Perio. & Rest. Dentistry, vol. 23, No. 3, 2003.

Kan, Joseph, Y.K., "Immediate Placement and Provisionalization of Maxillary Anterior Single Implants: A Surgical and Prosth. Rationale", Pract. Periodont Aesthet Dent, 2000.

Machine Design: "Robots are ready for medical manufacturing." Retrieved from MachineDesign.Com, <URL:http://machinedesign.com/article/robots-are-ready-for-medical-manufacturing-0712>, Jul. 12, 2007 (7 pages).

MedNEWS: "'Surgical Glue' May Help to Eliminate Suturing for Implants." Retrieved from MediNEWS.Direct, URL:http://www.medinewsdirect.com/?p=377, Dec. 21, 2007 (1 page).

Nevins, M. et al., "Histologic Evid. of a Connective Tissue Attachment to a Laser Microgrooved Abutments . . . ", The Int'l Jrnl of Perio. & Rest. Dentistry. vol. 30, No. 3, 2010.

Perry, Ronald D., Compendium, Clinical Materials Review, "Provisional Materials: Key Components of Interim Fixed Restorations", Jan. 2012.

Rossi, S; et al. "Pen-implant issue response to TiO2 surface modified implants", 2008, Blackwell Manksgaard, Turku, Finland.

Wohrle, Peter S., Single-Tooth Replacement in the Aesthetic Zone with Immediate Provisionalization: Fourteen Consecutive Case Reports, Pract Periodont Aesthet Dent, 1998.

"European Application Serial No. 15175921.4, Extended European Search Report mailed Jun. 1, 2016", 11 pgs.

"European Application Serial No. 15175921.4, Partial European Search Report mailed Feb. 4, 2016", 7 pgs.

\* cited by examiner

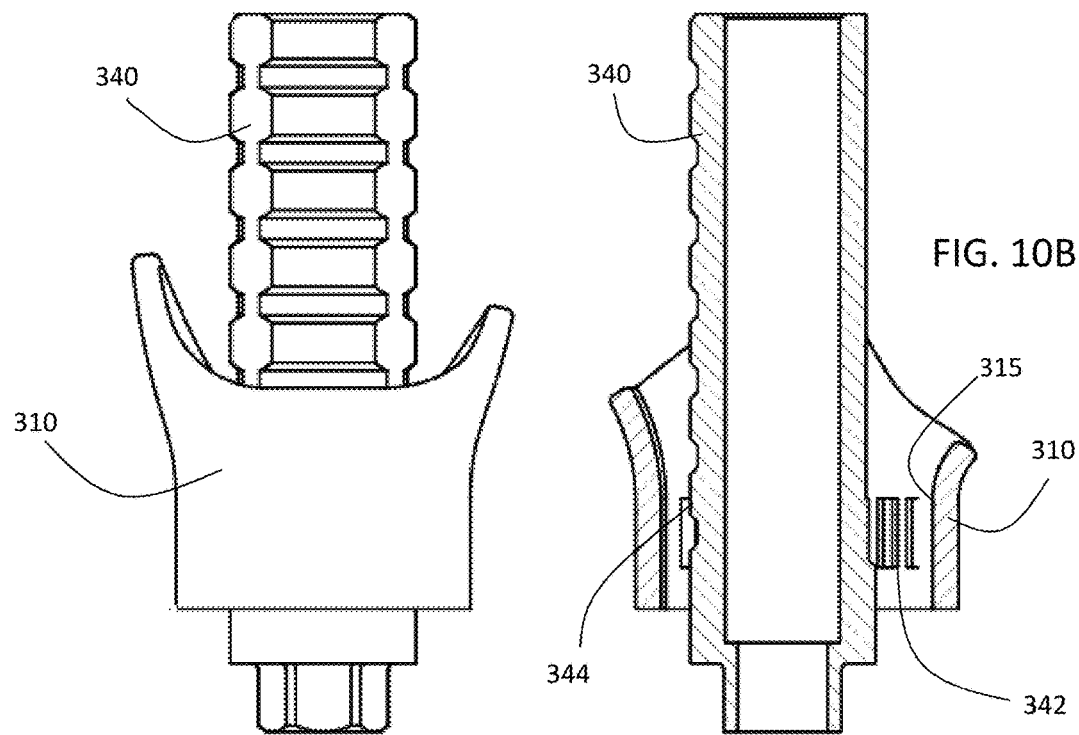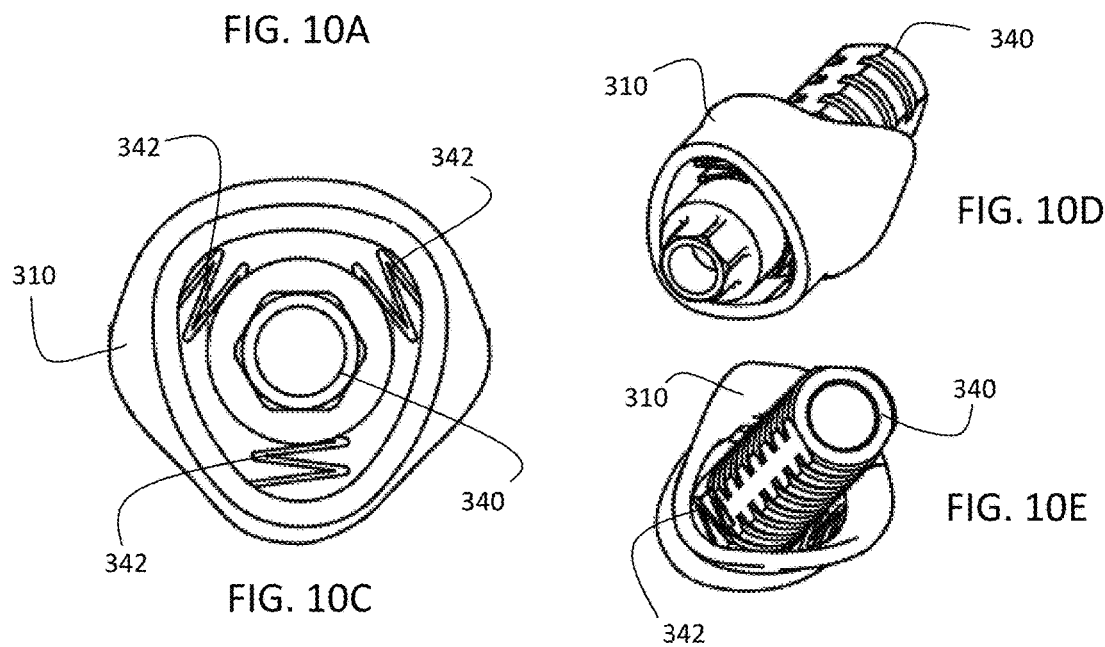

SOFT-TISSUE PRESERVATION ARRANGEMENT AND METHOD

FIELD OF THE INVENTION

The present invention relates generally to the field of dental implants and, in particular, to a new and useful soft-tissue preservation arrangement and method.

BACKGROUND OF THE INVENTION

The tooth is a structure of the oral cavity which is vital to the capability of chewing and important to the general well-being and appearance of people. Anatomically, the tooth resides within the oral cavity, firmly anchored within the upper and lower jaws (maxilla and mandible). Human teeth reside within two distinct anatomic regions of the jaws; the apical inferior portion of the tooth (the root) is connected to the jaw via an attachment called the periodontal ligament. This portion of the tooth that is connected to the bone can be defined as the "bone-zone" or hard tissue zone of the tooth. Second, the superior portion of the tooth (the anatomic crown) is connected to the jaw in the soft-tissue or gingival region of the jaw defined as the "tissue-zone" or soft tissue zone. The anatomic crown is demarcated as that portion of the tooth superior to the crest of bone and includes a small portion of the root superior to the crest of bone as well as the clinical crown that is visible. The tissue-zone forms a soft-tissue collar around the neck of a tooth. This tissue-zone connection (i.e. soft-tissue to tooth attachment) is composed of gingival fibers that insert into the superior aspect of the root surface; specifically, hemidesmosmal cell attachment to the root and crown forming a biological adhesion of the sulcular epithelium (gingival tissues) to the surface of a tooth.

The tissue-zone connection plays a critical role in maintaining health of the oral cavity. It does this by preventing the ingress of microbes and foreign substances into the body by providing a "biologic-seal" at the interface of the tooth-jaw connection at the tissue-zone. This functional attachment of the soft-tissue to the surface of the tooth should be fully appreciated as a critical defense barrier. As without the presence of this soft-tissue biologic seal the underlying bone would be vulnerable to numerous invasions of various foreign substances.

In addition, the tissue-zone plays an essential role in maintaining and preserving the dental esthetics of the smile. This same tissue-zone represents the peaks (papillae) and valleys of the soft-tissue gingival that surround the neck of each and every tooth. It is the spatial relationship of tooth form and color with healthy soft-tissue gingival architecture that are known as the essential building blocks of dental esthetics as we know it. Experts of dental esthetics have called the soft-tissue gingiva "the frame" of the picture, and regard the teeth as the "subject matter" of that painting. Disregarding the frame of a painting would certainly impact the overall esthetic appearance being viewed, and the same is true with respect to the gums and teeth. The loss or the alteration of anatomic structures of the tissue-zone has been shown to lead to an inferior esthetic outcome in addition to causing a potential risk of disease for the patient.

The tooth and its attachment to the jaw is subject to numerous pathogens over the lifetime of a patient, particularly due to trauma/fracture, endodontic failure, decay, localized periodontal disease, etc. Any of these conditions can lead to the eventual need for removal of either a single tooth or multiple teeth. The removal or extraction of a tooth or teeth will result in a radical morphologic change to the anatomy as well as the potential exposure of the internal tissues (connective tissues and underlying organs) of the body to invasion by foreign substances.

Loss of the biologic-seal of the tissue-zone also has a significant impact on soft-tissue changes to both the macro- and micro-anatomy of the gingiva. It is accepted in the dental literature that the loss of gingival attachment within the tissue-zone leads to the irreversible loss of the interdental papillae and the gingival architecture surrounding a tooth. Much effort has been directed toward preserving the bone after tooth removal but far less effort has been applied to preserving the macro- and micro-anatomy of the tissue-zone after tooth removal.

As will be explained more fully in the following, the method and arrangement of the present invention provide an effective means to preserve the esthetic and anatomic architecture of the tissue-zone after tooth removal and the immediate placement of a dental implant. In addition, the present invention simultaneously and effectively re-establishes the biologic-seal after tooth removal and immediate implant placement.

Immediate implant placement of a root-form dental implant has been shown to effectively osseointegrate. The residual gap that is present between the implant surface and the bone surface requires careful management whether a surgical flap is performed or a non-flapless minimally invasive extraction technique is used. In either of these two approaches, irreversible soft-tissue changes have been shown to occur with immediate implant placement after tooth removal. Changes within the tissue-zone are shown to occur as early as 2-3 days after the immediate implant placement.

SUMMARY OF THE INVENTION

According to one aspect of the present invention, a soft tissue preservation arrangement includes a hollow shell defining an interior volume extending from a proximal opening to a distal opening. The proximal opening is defined by a first perimeter that is smaller than a second perimeter defining the distal opening such that the shell tapers outwardly from the first perimeter to the second perimeter. The second perimeter is asymmetrically scalloped. The hollow shell either (1) is transparent or semi-transparent or (2) has a color configured to correspond to a color of a gingival tissue or a tooth.

According to another aspect of the invention, a dental restoration method includes extracting a tooth to form a bone socket and a soft tissue socket, inserting an implant into the bone socket, and coupling a post to the implant. The method also includes selecting a shell from a plurality of shells based on an analysis of the soft tissue socket. The shell defines an interior volume extending from a proximal opening to a distal opening. The proximal opening is defined by a first perimeter that is smaller than a second perimeter defining the distal opening such that the shell tapers outwardly from the first perimeter to the second perimeter. The second perimeter is asymmetrically scalloped. The hollow shell is transparent or semi-transparent. The method further includes placing the shell into the soft tissue socket such that the post extends in the interior volume of the shell. The shell is independently movable relative to the post. The method still further includes applying a luting compound to an interior space between an outer surface of the post and an inner surface of the shell so as to fixedly couple the shell to the post. The luting compound has a color corresponding to a color of the soft tissue socket or the tooth. The luting compound is visible through the shell.

According to yet another aspect of the invention, a soft tissue preservation arrangement includes a hollow shell defining an interior volume extending from a proximal opening to a distal opening. The proximal opening is defined by a first perimeter that is smaller than a second perimeter defining the distal opening such that the shell tapers outwardly from the first perimeter to the second perimeter. The second perimeter is asymmetrically scalloped. The arrangement also includes a post configured to be coupled to a dental implant, and a plurality of spokes adjustably coupling the post to the hollow shell. The plurality of spokes are configured to allow the shell to be adjustably moved relative to the post.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 10A is a side view of a post and a shell according to further aspects of the present invention.

FIG. 10B is a cross sectional view of the post and shell of FIG. 10A.

FIG. 10C is a bottom view of the post and shell of FIG. 10A.

FIG. 10D is a bottom perspective view of the post and shell of FIG. 10A.

FIG. 10E is top perspective view of the post and shell of FIG. 10A.

Figure 1:
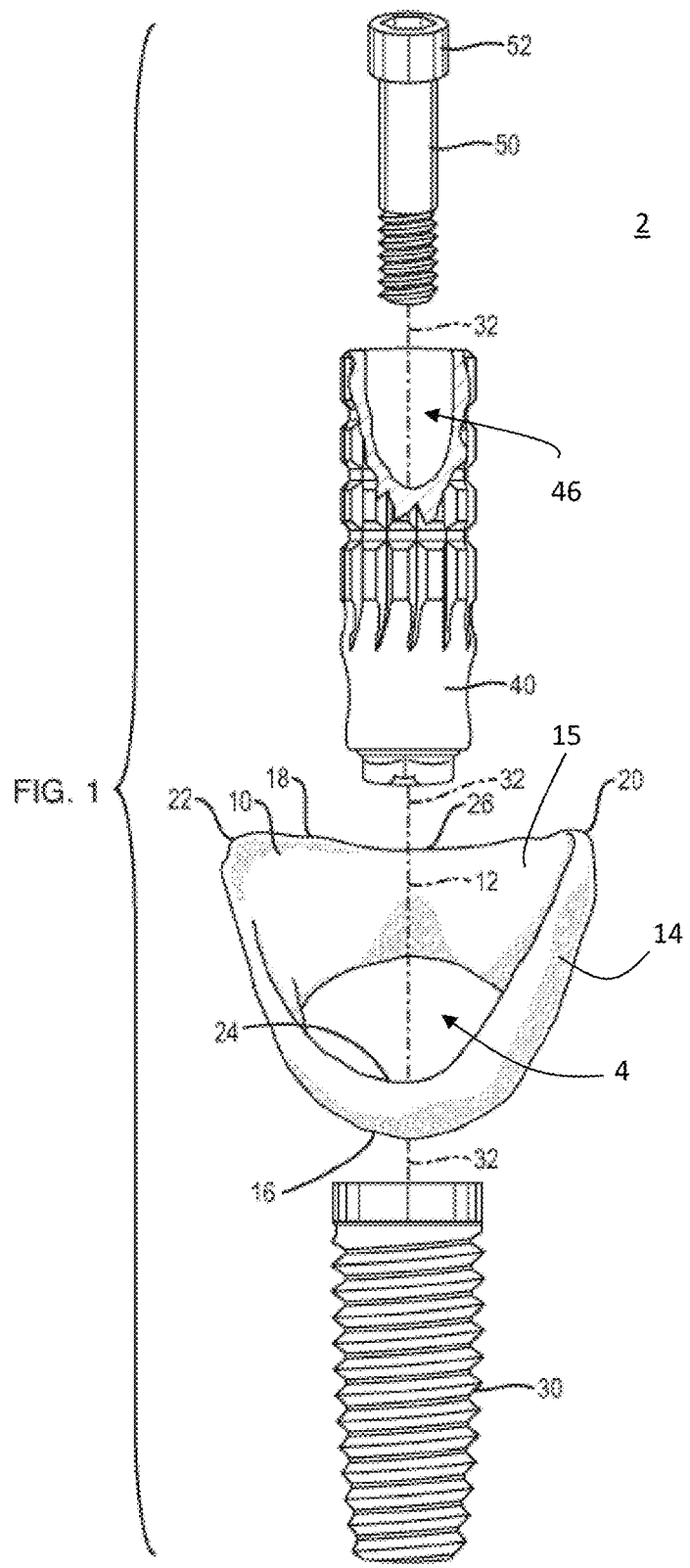
FIG. 1 is an exploded view of a soft-tissue preservation, dental implant arrangement according to some aspects of the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

FIG. 1 illustrates a soft-tissue preservation, dental implant arrangement 2 according to some aspects of the present invention. The arrangement 2 includes a hollow shell 10 with an interior volume 4 and a shell axis 12. The shell 10 has a lower first perimeter 16 adapted for placement toward the bone socket 102 (FIG. 6) of a lower mandibular, tooth. The first or inner perimeter 16 may be an upper perimeter if the shell 10 is to be used for replacing of an extracted upper or maxillary tooth so that terms like "upper" and "lower" as used herein are only relative terms and do not convey an absolute position or limitation.

The shell 10 also has a second or outer perimeter 18 adapted for placement adjacent an outer surface of the gingival tissue 108, around the soft-tissue socket 100. The first perimeter 16 is smaller than the second perimeter 18 so that the shell 10 tapers outwardly from the first perimeter 16 to the second perimeter 18 to anatomically mimic the shape of the soft-tissue socket 100 that remains immediately after a tooth has been extracted, and before the soft-tissue socket 100 starts to shrink or shift from the natural size, shape and position it had around the patient's natural tooth before extraction.

To further anatomically mimic the shape of the soft-tissue socket 100, the second perimeter 18 is also asymmetrically scalloped with a distal peak 20, a mesial peak 22 opposite the distal peak 20, a lingual valley 24 between the peaks 20, 22, and a facial valley 26 between the peaks 20, 22 opposite the lingual valley 24. The shapes, sizes, locations and heights of the peaks 20, 22 and valleys 24, 26 are selected to mimic different tooth types (e.g., maxillary or mandibular, central or lateral incisors, canines, premolars and molars) as described in greater detail below. The shell 10 is also sized for closely engaging against the soft-tissue socket 100 and mitigating gaps between the soft-tissue socket 100 and the shell 10. This sizing and shaping can be achieved by providing the practitioner with a set (i.e., a kit) of a plurality of shells 10 having different shapes, sizes and types so that a shell 10 can be selected based on patient-specific conditions to closely fit and engage the soft-tissue socket 100 without gaps and, thus, form a biological or biologic-seal inhibiting ingress of contaminants to the soft-tissue socket 100 and the underlying bone socket 102.

The arrangement 2 also includes a dental implant 30 having an implant axis 32. The dental implant 30 is configured for placement in the bone socket 102 immediately after tooth extraction. It should be understood that, prior to placement of the dental implant 30, the bone socket 102 can be cleared and dressed, for example, by removing debris and drilling a bore in the bone socket 102. As non-limiting examples, the implant 30 can be made of surgical steel or other metals such as titanium/titanium alloy.

The arrangement 2 further includes a temporary post 40 configured to be coupled to the dental implant 30 in coaxial alignment. For example, the temporary post 40 can be coupled to the dental implant 30 by a screw 50 that is inserted into a central bore 46 in the post 40 and screwed into a treaded bore in the implant 30 such that a head 52 of the screw 50 can engage an annular step in the post 40. As non-limiting examples, the post 40 can be made of steel (e.g., stainless steel), titanium, polyether-ether-ketone (PEEK), ceramic or other durable material such as gold alloy, e.g. AuPdAg (gold-palladium-silver).

As will be described in detail below, the shell 10 is placed in the soft-tissue socket 100 with a freedom of motion in the x-, y- and z-directions and with freedom of rotation about all three axes. According to some aspects of the present disclosure, this freedom of motion is achieved by mechanically de-coupling the shell 10 from the implant 30 (which is rigidly fixed in the bone socket 102 at its own angle and depth) or the post 40. According to alternative aspects of the present disclosure described below with respect to FIGS. 10A-14B, the shell 10 is adjustably coupled to the post 40 by a plurality of spokes 342 that allow for independent positioning and orientation of the shell 10 relative to the post 40. In either case, the post 40 extends from the implant 30 through the interior volume 4 of the shell 10 when the implant 30 is placed in the bone socket 102, the shell 10 is placed in the soft-tissue socket 100, and the post 40 is coupled to the implant 30. Also, in either case, the position and orientation of the shell 10 can be adjusted with respect to the implant 30 such that the positions and orientations of the shell 10 and the implant 30 (and, thus, the post 40) can be independently determined based on the soft-tissue socket 100 and the bone socket 102, respectively, when the implant 30 is placed in the bone socket 102, the shell 10 is placed in the soft-tissue socket 100, and the post 40 is coupled to the implant 30. In other words, the shell 10 and the implant 30 can be independently positioned and oriented in the soft-tissue socket 100 and the bone socket 102, respectively, without requiring alignment of the shell axis 12 and the implant axis 32.

The arrangement 2 still further includes a luting compound 60 (shown in FIGS. 6 and 8) configured to fixedly couple the shell 10 to the post 40 once the shell 10 and the implant 30 have been placed in the soft-tissue socket 100 and the bone socket 102, respectively. The luting compound 60 can be initially fluid such that the luting compound 60 can be filled into an interior space between the shell 10 and the temporary post 40 and allowed to set solid. In the illustrated example of FIGS. 1-6 and 8, only then is the shell 10 fixed to the post 40 and the implant 30, with no other previous connection between the shell 10 and the implant 30 so that an outer surface 14 of the shell 10 engages against the soft-tissue socket 100 without gaps and without requiring any alignment between the shell axis 12 and the implant axes 32. The luting of the shell 10 to the post 40 forms a temporary soft-tissue-preservation abutment, which can be removably coupled to the implant 30 (e.g., via the screw 50).

Figure 6:
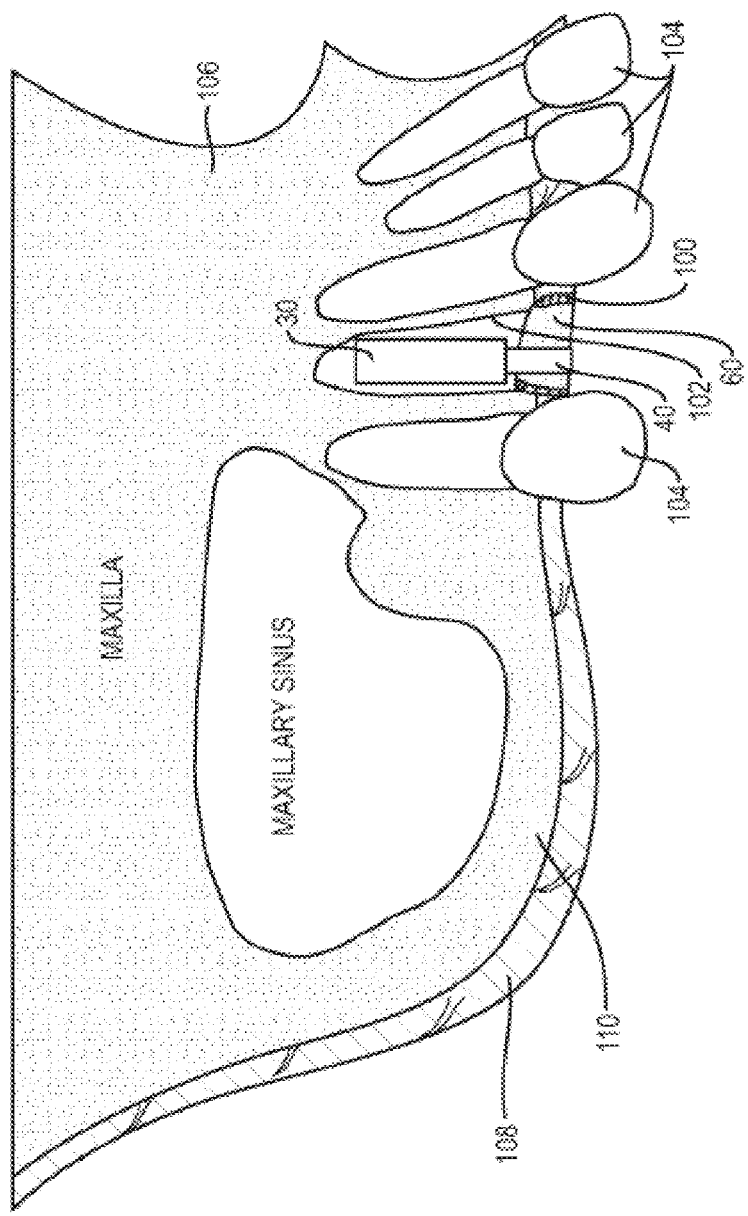
FIG. 6 is a sectional view of the soft-tissue preservation, dental implant arrangement of FIG. 1 after a luting compound has been applied.

The application of the luting compound 60 also seals the bone socket 102 in the jaw bone 106, which, in the case of FIG. 6, is the maxilla that is shown to have other teeth 104 on opposite sides of the extracted tooth socket 102. An inner surface 15 of shell 10 can be configured to facilitate adherence of the luting compound 60 to the inner surface 15. According to some aspects, to improve such adherence, the inner surface 15 can be treated, e.g. by roughening its texture.

As described above, a kit including a plurality of shells 10 can be provided to facilitate the selection of a shell 10 based on one or more patient specific conditions (e.g., a type of tooth to be replaced, a size of the soft-tissue socket 100, a shape of the soft-tissue socket 100, etc.) to closely fit and engage the soft-tissue socket 100. By selecting and placing an appropriate shell 10 from the kit into a patient's soft-tissue socket 100, the soft-tissue gingival architecture can be preserved, a biological or biologic-seal can be formed, and/or bone regenerative materials can be retained.

Figure 3:
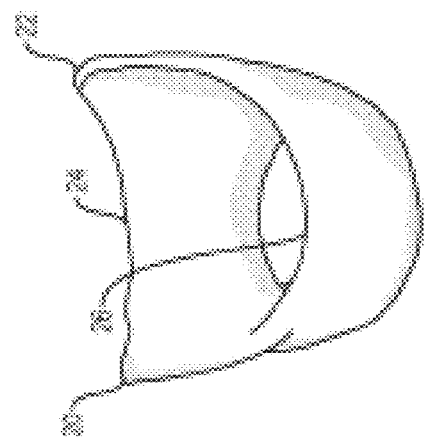
FIG. 3 is a perspective view of a shell according to additional aspects of the present invention.
Figure 5:
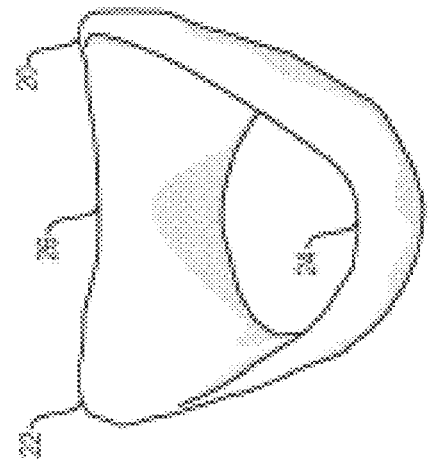
FIG. 5 is a perspective view of the shell shown in FIG. 1.
Figure 2:
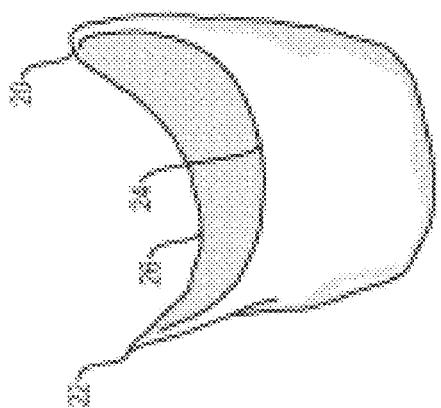
FIG. 2 is a perspective view of a shell according to some aspects of the present invention.
Figure 4:
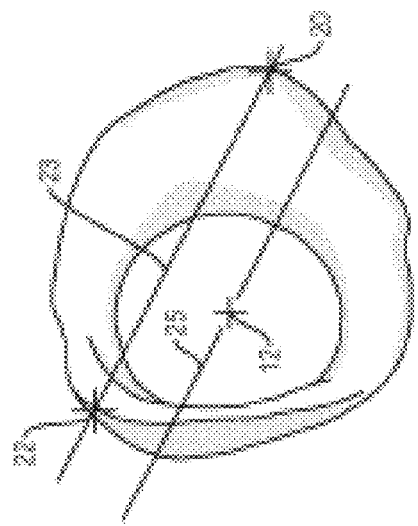
FIG. 4 is a perspective view of a shell according to further aspects of the present invention.

The plurality of shells 10 that make up the kit can have a plurality of different dimensions and/or shapes. According to some aspects of the present disclosure, the shells 10 in the kit can be configured to replace different, specific types of teeth. For example, in FIGS. 1 and 5, the lingual valley 24 is lower than the facial valley 26 for mimicking maxillary and mandibular incisors. For mimicking maxillary and mandibular canines, the lingual valley 24 and the facial valley 26 can be of substantially equal height as illustrated, for example, in FIG. 2. For premolars and molars, the opposite of incisors is true so that, as shown in FIG. 3, the lingual valley 24 can be higher than the facial valley 26 and mesial and distal peaks 20 and 22 are not as highly scalloped as in incisors. Also, for some tooth types, the distal and mesial peaks 20 and 22, as shown in FIG. 4, are not in a common plane 23 with the plane 25 extending through the shell axis 12. The asymmetry can be also selected to more closely mimic the true shape and size of a soft-tissue socket 100 before it starts to deteriorate. It should be understood that these shapes are merely examples and not absolute rules since there can always be exceptions and variations to the rules as dental anatomy varies and may sometimes reside outside the norms. The kit of shells 10 in various sizes, types and shapes provided to the practitioner can accommodate these variations by allowing the practitioner to select a shell 10 for a different tooth replacement type.

According to a non-limiting implementation, the plurality of shells 10 provided in the kit can include a series of different tissue-zone heights ranging from approximately 2 mm to approximately 5 mm and a plurality of root form configurations with a plurality of horizontal widths. To further illustrate, the following are non-limiting examples of shapes, sizes, and/or dimensions for a plurality shells 10 from which a kit may be comprised:

Maxillary Right Central Incisor: Height 2 mm, Height 3 mm, thru 5 mm. Diameter, Small, Medium and Large. An irregular superior surface is provided to conform to the soft-tissue gingival architecture. The interproximal points can be longer in dimensions then the labial and lingual surfaces. The inner shell allows for the eccentric position of the shell 10 over the center axis of the implant 30 held within the bone 102.

Maxillary Right Lateral Central Incisor: Height 2 mm, Height 3 mm, thru 5 mm. Diameter, Small, Medium and Large. An irregular superior surface is provided to conform to the soft-tissue gingival architecture. The interproximal points can be longer in dimensions then the labial and lingual surfaces. The inner shell allows for the eccentric position of the shell 10 over the center axis of the implant 30 held within the bone 102.

Maxillary Right Canine: Height 2 mm, Height 3 mm, thru 5 mm. Diameter, Small, Medium and Large. An irregular superior surface is provided to conform to the soft-tissue gingival architecture. The interproximal points can be longer in dimensions then the labial and lingual surfaces. The inner shell allows for the eccentric position of the shell 10 over the center axis of the implant 30 held within the bone 102.

Maxillary Left Central Incisor: Height 2 mm, Height 3 mm, thru 5 mm. Diameter, Small, Medium and Large. An irregular superior surface is provided to conform to the soft-tissue gingival architecture. The interproximal points can be longer in dimensions then the labial and lingual surfaces. The inner shell allows for the eccentric position of the shell 10 over the center axis of the implant 30 held within the bone 102.

Maxillary Left Lateral Central Incisor: Height 2 mm, Height 3 mm, thru 5 mm. Diameter, Small, Medium and Large. An irregular superior surface is provided to conform to the soft-tissue gingival architecture. The interproximal points can be longer in dimensions then the labial and lingual surfaces. The inner shell allows for the eccentric position of the shell 10 over the center axis of the implant 30 held within the bone 102.

Maxillary Left Canine: Height 2 mm, Height 3 mm, thru 5 mm. Diameter, Small, Medium and Large. An irregular superior surface is provided to conform to the soft-tissue gingival architecture. The interproximal points can be longer in dimensions then the labial and lingual surfaces. The inner shell allows for the eccentric position of the shell 10 over the center axis of the implant 30 held within the bone 102.

It should be understood that the kit can include any combination of two or more of the above example shells 10, or other shells 10 having different shapes, sizes, and/or dimensions than the examples described above. According to additional and/or alternative aspects of the present disclosure, the kit can also include one or more luting compounds 60, plugs 80, and/or tooth form temporaries 70 described in greater detail below. It is contemplated that the dimensions and shapes of the shells 10 provided in the kit can be based on an analysis (e.g., a statistical analysis) of a plurality of soft-tissue sockets 100 remaining after tooth removal. Additionally, it should be understood that, according to additional and/or alternative aspects of the present disclosure, the shell 10 can be custom made shell 10 for a particular patient.

One of the functions of the shell 10 is to preserve the esthetics of the gingival tissue. However, it has been discovered that when the shell 10 is installed, a portion of the shell 10 may remain visible above the gingival tissue under some circumstances. The color discrepancy between the shell 10 and the adjacent teeth, gingival tissue, and/or dental prosthesis (e.g., an attached tooth-form such as the type described and illustrated for FIG. 7) negatively impacts the esthetics. According to some aspects of the present invention, one approach for addressing such problems is to make the shell 10 from a material having a color that mimics (i.e., generally corresponds to) the color of the adjacent teeth, gingival tissue, and/or dental prosthesis. For example, the shell 10 can be configured to mimic the color of an adjacent tooth, gingival tissue, or dental prosthesis by selecting a material for the shell 10 based on techniques employed in cosmetic dentistry for final prosthesis color matching. As non-limiting examples, the shell 10 can be configured to have a color for approximating the color of a patient's gingival tissue (e.g., pale pink, coral pink, light brown, dark brown, etc.) using PEEK, titanium (e.g., anodized titanium), Polyoxymethylene (POM) (e.g., DELRIN), 3D printable materials, and/or the like. While this approach may be effective, it can be challenging or impractical to manufacture such shells 10 on a commercial scale due to the wide variety of colors that may be required to effectively tailor the shell 10 to individual patient conditions.

Another approach of the present invention obviates those challenges and difficulties. According to alternative aspects of the present invention, the shell 10 can be made from a transparent material and the luting compound 60 can be made from a material configured to have a color that mimics (i.e., generally corresponds to) the color of the teeth, the gingival tissue, and/or the dental prosthesis at or adjacent to the implantation site. Accordingly, if a portion of the shell 10 extends above the soft-tissue socket 100, the exposed portion of the shell 10 appears to be the color of the luting compound 60 due to the transparency of the shell 10. Advantageously, the shells 10 can thus be manufactured on a commercial scale from a common, transparent material(s) and then the luting compound 60 can be custom made or altered according to the specific conditions of each patient. Because the luting compound 60 can be more readily manufactured than the shell 10, this approach can provide a more practical and commercially viable approach to customized color matching for the arrangements and methods of the present invention. Indeed, in some instances, the luting compound 60 can be manufactured locally (e.g., chair-side) by a patient's treating clinician for example. As such, the shell 10 and/or luting compound 60 can improve preservation of the natural soft tissue architecture and provide a biologic seal without compromising esthetics.

Non-limiting examples of suitable materials having transparency (i.e., semi-transparent or fully transparent) for making the shell 10 include poly(methyl methacrylate) (PMMA) (e.g., USP Class VI), polycarbonate, polysulfone, combinations thereof, and/or the like. As additional non-limiting examples, the shell 10 can be made from a material configured to resorb such as, for example, LACTOSORB manufactured by Biomet 3i (Palm Beach Gardens, Fla.).

The luting compound 60 can be made from materials configured to have a color that mimics or approximates the colors of the adjacent teeth, gingival tissue, and/or dental prosthesis of the patient. For example, the color of the healthy gingiva can vary between pale pink, coral pink, light brown, dark brown and other colors depending on a variety of patient specific factors such as the amount of physiological melanin pigmentation in the patient's epithelium, the degree of keratinization of the epithelium, and/or the vascularity and fibrous nature of the underlying connective tissue pigmentation. Similarly, for example, the color of the adjacent teeth and/or dental prosthesis can have a wide variety of shades and colors from white to reddish brown, yellow, reddish yellow, or gray. According to aspects of the present disclosure, the luting compound 60 can be made from one or more materials and/or additives in various compositional proportions selected based on an analysis of a patient's conditions, e.g., using shade guides and/or photography. As non-limiting examples, the luting compound 60 can made from polymerization materials (e.g., a composite, acrylic, resin, etc.)

It is contemplated that, according to some aspects of the present disclosure, the clinician can custom make the luting compound 60 based on the analysis of the patient conditions. According to additional and/or alternative aspects, the clinician can select a luting compound from a plurality of premade luting compounds 60 based on the analysis of the patient conditions. It should be understood that, according to some additional and/or alternative aspects of the present disclosure, the kit of shells 10 described above can include a plurality of different luting compounds 60 having a plurality of different colors as well. Alternatively, a plurality of different premade luting compounds 60 having a plurality of different colors can be provided as a separate luting-compound kit.

Figure 8:
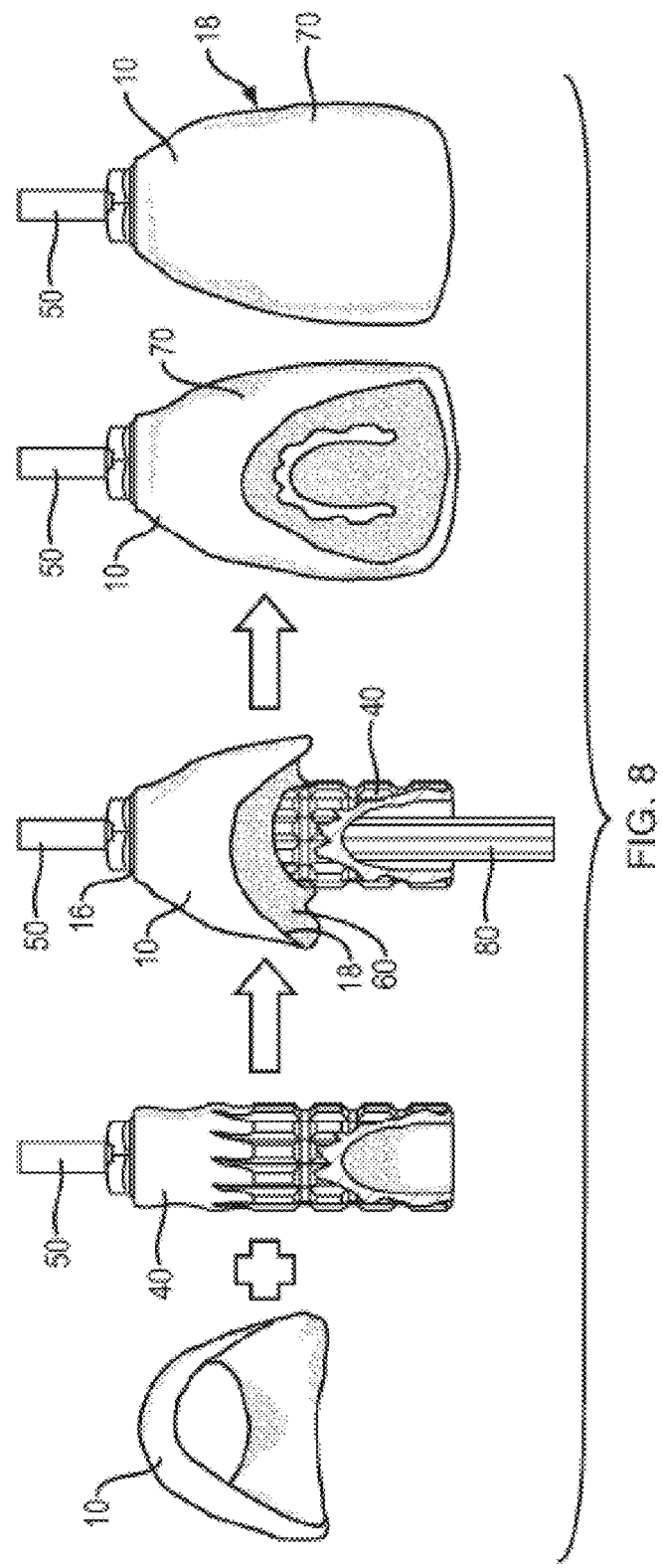
FIG. 8 is a composite view of parts of a soft-tissue-preservation abutment in a sequence showing an assembly of the parts of the abutment according to some aspects of the present invention.
Figure 9:
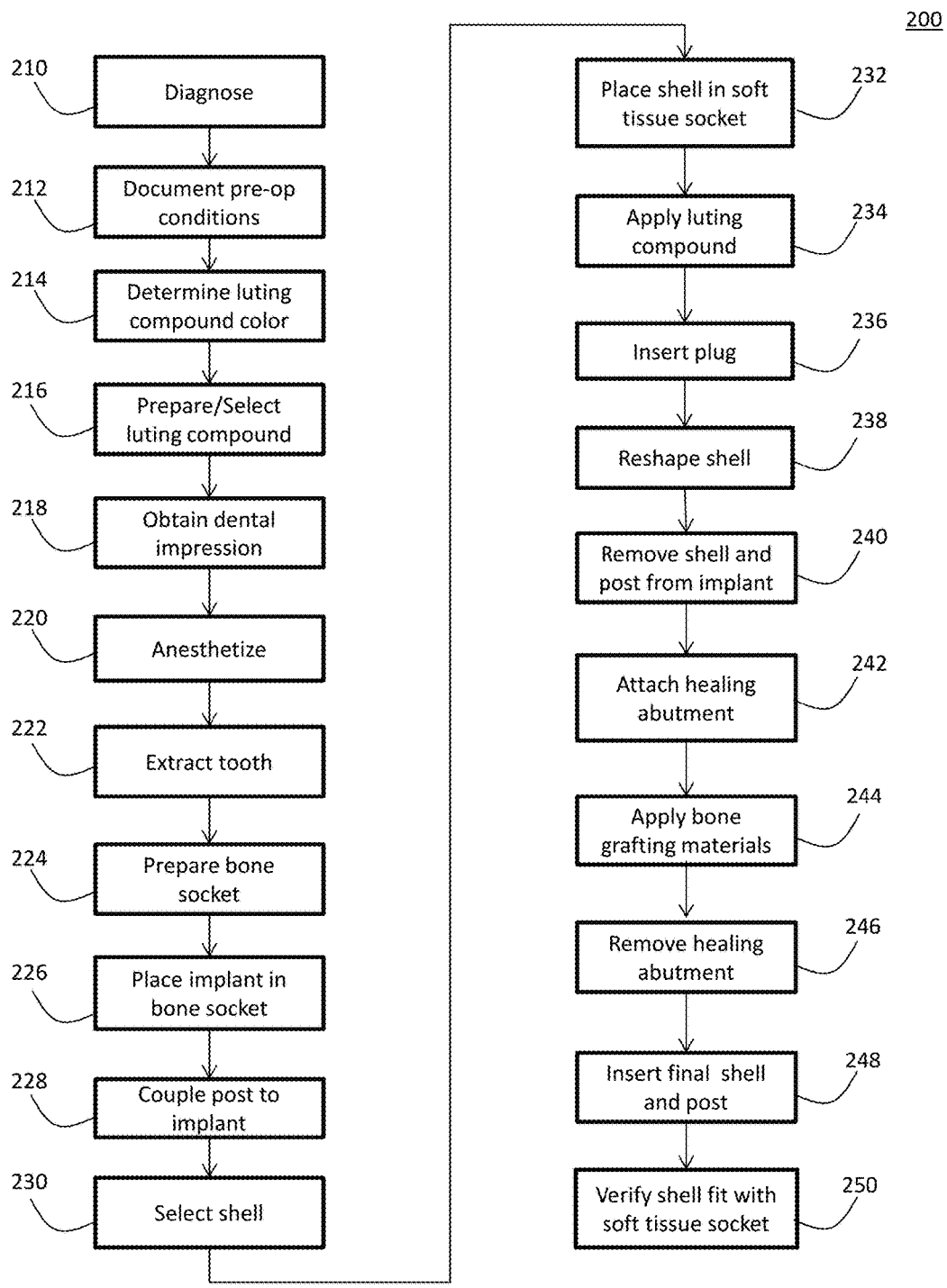
FIG. 9 is a flowchart for a process of employing a shell to form a soft-tissue preservation, dental implant arrangement according to some aspects of the present invention.
Figure 11A:
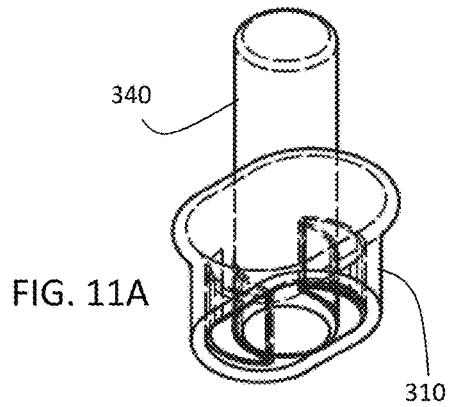
FIG. 11A is a perspective view of a shell and a post connected by a first type of spoke according to additional aspects of the present invention.
Figure 12A:
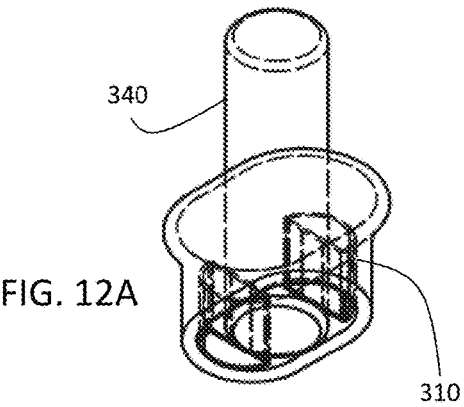
FIG. 12A is a perspective view of a shell and a post connected by a second type of spoke according to additional aspects of the present invention.
Figure 11B:
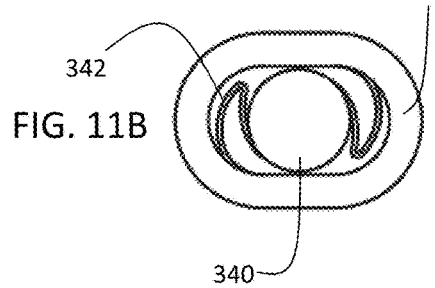
FIG. 11B is a bottom view of the shell and the post connected by the first type of spoke from FIG. 11A
Figure 12B:
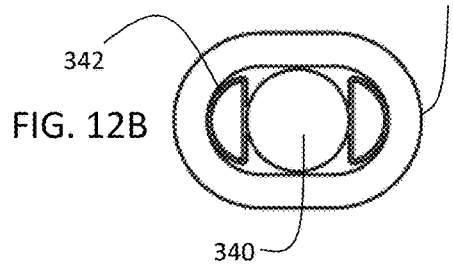
FIG. 12B is a bottom view of the shell and the post connected by the second type of spoke from FIG. 12A.
Figure 13A:
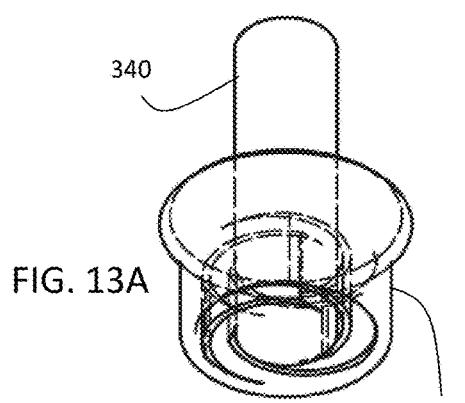
FIG. 13A is a perspective view of a shell and a post connected by a third type of spoke according to additional aspects of the present invention.
Figure 14A:
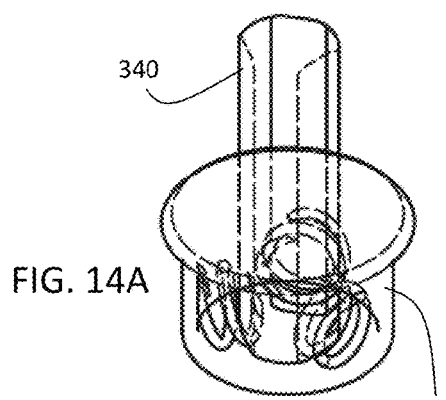
FIG. 14A is a perspective view of a shell and a post connected by a fourth type of spoke according to additional aspects of the present invention.
Figure 13B:
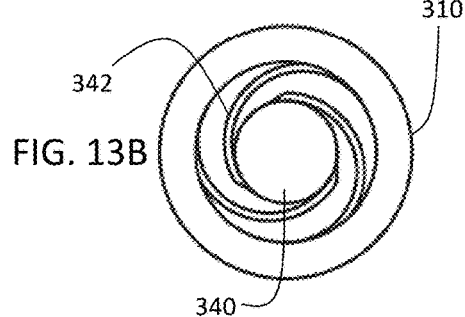
FIG. 13B is a bottom view of the shell and the post connected by the third type of spoke from FIG. 13A.
Figure 14B:
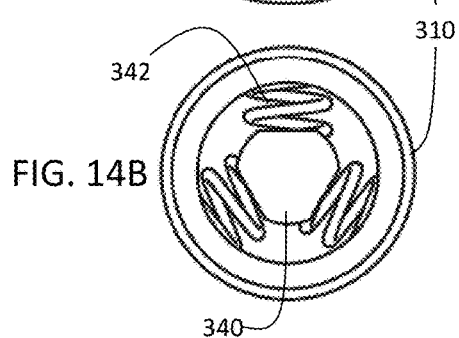
FIG. 14B is a bottom view of the shell and the post connected by the fourth type of spoke from FIG. 14A.

Referring now to FIGS. 6, 8 and 9, an example process 200 is illustrated for employing the shell 10 to preserve the soft-tissue socket 100 and provide a biologic seal after tooth extraction according to aspects of the present disclosure. In particular, the example process 200 employs the shell 10 to form a temporary soft-tissue-preservation, dental implant arrangement 2. While the process 200 is described below for the extraction and replacement of a single tooth, it should be understood that the described method is not limited to a singular tooth and can be employed for multiple teeth according to additional and/or alternative aspects of the present disclosure.

At step 210, the diagnosis that a tooth requires extraction is determined by a dental clinician. The diagnosis can be performed, for example, based on clinical examination, radiographic analysis, detailed past dental history, review of signs and symptoms, combinations thereof, and/or the like.

At step 212, prior to the extraction of the tooth a clinical photo can be taken to allow future comparison of the pre-treatment condition that was present versus the post-operative outcome after treatment is completed. The photo may have a reference measurement tool or instrument so that detailed analysis of the soft-tissue changes can be analyzed.

At step 214, a color for the luting compound 60 can be determined to color match the luting compound 60 to the environment in which the shell 10 will be utilized. In particular, the color of the luting compound 60 can be determined from a plurality of different potential colors based on an analysis of the patient's teeth and/or gingival tissue (i.e., patient specific conditions). For example, an analysis of a patient's teeth and/or gingival tissue can be conducted using shade guides and/or the photos obtained at step 212.

After the color of the luting compound 60 is determined at step 214, the luting compound 60 can be prepared or selected at step 216. In one non-limiting example, a plurality of different luting compounds 60, each having a different color, can be provided as a luting-compound kit such that one of the plurality of luting compounds 60 in the luting-compound kit is selected based on the analysis at step 214. In another non-limiting example, the luting compound 60 can be made from one or more materials and/or additives in various compositional proportions selected based on the analysis at step 214. In either case, the prepared/selected luting compound 60 is configured to have a color that substantially matches or mimics the gingival tissue and/or teeth of the patient. It is contemplated that, according to some aspects, the luting compound 60 can alternatively have a color that substantially matches or mimics the color of a dental prosthesis that may be employed in conjunction with the shell 10 as described in greater detail, for example, with respect to FIG. 7 below.

At step 218, a dental impression can be obtained by using impression materials such as, for example, alginate, polyether, vinyl polysiloxane, and other materials to establish an accurate representation of the teeth and surrounding gingival tissues. According to additional and/or alternative aspects, the dental impression can be performed using a digital impression such as, for example, cone beam computer tomography or digital oral impression (CAD/CAM Digital Impressions) using a hand-held oral scanning device of known design.

At step 220, an area of the mouth in which the tooth is to be extracted is anesthetized with a dental local anesthetic solution. A local anesthetic solution can be delivered to the area either as a local infiltration dental injection or as a regional nerve block to the area. The patient can be given adequate time (e.g., 5 minutes) for the dental local anesthetic to anesthetize the region of the mouth that is being treated.

At step 222, the tooth is extracted by a technique that preserves the entire tissue-zone and minimizes trauma to the supporting gingival tissues 106. For example, to preserve the soft-tissue architecture of the immediate and surrounding gingival, a flapless surgical technique can be used to extract the tooth. The flapless surgical technique can include first incising the entire supra-crestal attachment of the tooth 360 degrees around the tooth (i.e., around soft-tissue socket 100) to disconnect the soft-tissue attachment fibers. This can be accomplished, for example, using a surgical blade, piezo-surgical instrument, micro-rotary dental handpiece or dental laser soft-tissue cutting instrument.

The flapless surgical technique can also include dissection of the supra-crestal attachment which includes the sucular epithelium, junctional epithelium, connective tissue inserting fibers which are found between the connective tissue and the surface of the root above the crest of bone 110. Once the supra-crestal fibers are released the superior periodontal ligament fibers (attachment fibers found between the alveolar bone socket 102 and root surface) can next be incised. The superior periodontal fibers attach the surface of the tooth (cementum) to the inner bony socket can also be severed using minimal disruption to the surrounding soft-tissue and bony architecture. This can be accomplished by, for example, using micro-surgical instruments, periotomes, a rotary diamond pointed diamond, piezeo-surgical instrument, laser. The instrument diameter can be between approximately 20 microns to approximately 50 microns (or approximately ⅛ to ¼ millimeter in diameter) as this is the typical dimension of the width of the periodontal ligament space. The surgical instrument is placed into the entrance of the periodontal ligament between the tooth 104 and inner socket wall 100. The periodontal attachment fibers are served around the tooth to a depth of approximately 1 to approximately 4 millimeters, depending on ease of entry into the periodontal ligament space.

The extraction of the tooth can be first initiated using a rotational movement in order to sever the remaining sub-crestal periodontal fibers attaching the tooth to the inner socket wall. This can be performed with either using a reduced diameter elevator, periotome or extraction forceps. Once a rotational movement is achieved a vertical force can be applied to the tooth to advance the root out of the bone socket 102.

When the extraction is performed using this example flapless technique, minimal disruption can occur to the surrounding soft-tissues of the gingival. The interdental papillae may not be surgically altered from the pre-treatment condition. Incisors may not be made which compromise the blood supply to the region of the bone or surrounding soft-tissue gingival. The architecture of the soft-tissue has not been substantially altered other than the severing of the attachment fibers between the root surface and inserting fibers. It should be understood that, according to alternative aspects of the present disclosure, the tooth can be extracted using other techniques.

At step 224, any inflammatory granulation tissue can be removed from within the bone socket 102, if necessary. This can be performed using a small sized circular curette. Inspection can be performed to ensure the integrity of the remaining inner socket walls 100. A radiograph may be taken to determine the remaining configuration of the tooth socket. This step can also be referred to as preparing the bony socket or bone socket 102.

At step 226, a dental implant 30 is immediately placed within the residual extraction socket 102. The term "immediately" as used herein means that the implant 30 is placed shortly after the bone socket 102 has been fully prepared to receive the implant 30 (e.g., within approximately 30 minutes) during the same patient's visit. For example, the implant 30 can be placed (vertically) at the level of the remaining crest of bone 110. Since the remaining crest of bone 110 has different heights the implant 30 may be slightly supra-crestal at one region and slightly subcrestal at another region of the bone socket 102. Additionally, for example, the implant 30 can be further placed (horizontally) with an axial position allowing for a screw-retained temporary. The center axis of the implant 30 may be therefore placed in the position of the cingulum of the adjacent teeth (i.e., positioning the implant 30 toward the palatal (lingual) aspect of the residual extraction socket 102). Positioning the implant 30 biased toward the palatal (lingual) position of the extraction socket 102 facilitates use of a screw-retained immediate temporary restoration.

This advantageous placement of the implant 30 is made possible by the fact that the shell 10 is mechanically decoupled from the implant 30 (e.g., FIGS. 1-6 and 8) or otherwise allows for a range of relative movement (e.g., FIGS. 10A-14B) and, thus, the shell 10 need not be affixed with respect to the axis or position of the implant 30 as has been common in the past. While the embodiment described above employs a screw 50 for retaining the post 40 to the implant 30, according to alternative implementations, the immediate temporary can be configured to be cemented to the substructure directly and place the location of the micro gap below the soft tissue zone.

The implant 30 can mechanically engage and lock into a portion of the bone. According to some aspects, this may be achieved at the apical end of the implant 30. Additionally and/or alternative, the mechanical engagement and locking to the bone can be achieved on a lateral portion of the exterior of the implant 30.

According to aspects of the present disclosure, the diameter of the implant 30 is smaller than the greatest diameter of the root of the tooth that was removed. Therefore, the dissimilar diameters between the implant 30 and the residual bony tooth socket 102 result in a "gap" or space between the residual bony socket 102 and the exterior surface of the implant 30 as shown, for example in FIG. 6. The gap allows a bone regenerative material to be placed between the implant surface and the inner tooth socket buccal plate. The gap also allows for future bone regeneration via the in growth of the blood supply and new osteoblasts. It is important not to use an implant diameter that would make direct contact to the labial plate of bone as this would compromise the blood supply that is needed to preserve the labial (buccal) plate of bone as the implant surface provide no ability for angiogenesis. According to aspects of the process 200, the preservation of the overlying gingival and surrounding soft-tissues is preserved, at least in part, by several factors: (1) a minimally invasive surgical approach; (2) a shell 10 configured to preserve the soft-tissue architecture; and (3) preservation and promotion to re-establish the blood supply to the surrounding tissues.

At step 228, a screw-retained temporary post 40, such as the PreFormance Post from Biomet 3i Dental Implants of Palm Beach Gardens, Fla., is coupled to the dental implant 30 held within the bone 102. It is contemplated that, according to alternative aspects, other posts 40 can be employed (e.g., a cement retained post).

At step 230, a shell 10 is selected according to patient-specific conditions (e.g., for the proper vertical and horizontal dimensions) as described above. Also, as described above, the shell 10 can be supplied in a plurality of different shapes and/or dimensions for selection based on the tooth to be replaced (e.g., as a kit).

At step 232, the selected shell 10 is placed in the soft-tissue socket 100. As described above, the shell 10 is eccentrically positioned relative to the implant 30 so that an outer surface 14 of the shell 10 makes physical contact with the soft-tissue socket 100, achieving a biologic-seal between soft-tissue socket 100 and the shell 10. To that end, the inferior end (i.e., the first perimeter 16) of the shell 10 can be placed into the soft-tissue socket 100 to make direct contact with the implant head platform of the implant 30 within the bone 106. The superior end (i.e., the second perimeter 18) can approximate the free-gingival margin of the surrounding tissue-zone. The outer surface 14 of the shell 10 makes direct contact with the inner soft-tissue residual socket 100. Thus, the final adapted shell 10 substantially inhibits (or completely eliminates) any openings and gaps between the soft-tissue socket 100 and the surrounding gingival 108. As a result, a biologic-seal to the underlying tissues below the surface is re-established.

Re-establishing the biologic seal can also provide containment and protection for any bone regenerative materials placed between the surface of the bone socket 102 and the surface of the implant 30 filling the "gap" between the dissimilar diameters of these two structures. If necessary a membrane (not shown) can be placed at the level of the bony crest 110 and placement of the shell 10 will provide complete coverage of the membrane below providing a biologic-seal to the outer oral environment.

The outer surface 14 of the shell 10 promotes soft-tissue adhesion to the shell 10. According to some additional and/or alternative aspects of the present invention, the outer surface 14 of the shell 10 can have a plurality of distinct surface texture regions. For example, a superior (gingival) surface region can be smooth to discourage the accumulation of plaque and an inferior region can have an ordered microgeometric repetitive surface texture or pattern. The superior smooth zone can extend 1 mm to 3 mm. The inferior textured region can cover the remaining outer surface 14 of the shell 10. The textured surface of the inferior region encourages the re-establishment of the gingival fibers to make contact and adhere to the surface of the shell 10. For example, the textured surface can have a regular microgeometric pattern that is uniform. It is also contemplated that the surface texture can be modified chair-side using a rotary instrument, such as a uniquely designed dental bur, that results in a ordered micro-geometric repetitive surface pattern in the form of alternating ridges and grooves, each having an unfixed width in an alternating range of about 2 to about 25 microns (micrometers) and a non-fixed or altering depth in a range of about 10 microns to about 50 microns.

The surface texture is not limited to two or more texture patterns, it is conceivable that the surface of the shell 10 be design with a single texture covering the entire outer surface 14 or designed from multiple textures to encourage direct soft-tissue adaptation within the tissue-zone. A smooth surface at the superior regions discourages plaque accumulation while the textured surface promotes and accelerates effective soft-tissue adhesion. The surface textures described above have been shown to promote soft-tissue preservation in combination with providing an effective biologic-seal of the surface of the shell 10 to the residual soft tissues.

At step 234, the luting compound 60 is employed to fixedly couple the shell 10 to the post 40 (e.g., via a chair-side technique). Generally, the entire inner surface 15 of the shell 10 is filled with the luting compound 60 as shown in FIGS. 6 and 8, minimizing or eliminating voids or gaps within the luting compound 60.

According to some aspects, the post 40 can include a bore 46 to provide access to the screw 50 and allow for removal of the shell 10 and post 40 from the implant 30. At step 236, a plug 80 can be inserted into the bore 46 of the post 40, as shown in FIG. 8, for final finishing and temporary insertion. The plug 80 is used to temporarily plug the bore 46 of the post 40 before the luting step so that access to a head 52 of a screw 50 can be reestablished when a permanent tooth replacement is to be attached to the implant 30, or at other points in the process 200, by extracting the plug 80. As one non-limiting example, the plug 80 can be cylindrical shaped and made from nylon.

In certain situations it may be necessary to modify the shape of the shell 10 to properly adapt the shell 10 to the soft-tissue socket 100. Accordingly, at step 238, the shell 10 can be reshaped if necessary. For example, an additive technique of material or a subtractive technique can be employed in which additional materials are added to the shell 10 or a portion of the shell 10 is removed.

To resurface the shell 10, a surface texture bur attached to a standard rotary handpiece can be utilized. The surface texture bur can be designed to re-establish the surface texture that was created in the texture zone on the outer surface 14 of the shell 10. For example, the surface texture bur can be a rotary bur that is designed to provide a microgeometric repetitive surface pattern forming a varying widths and varying depths ranging from about 10 microns to about 50 microns. The irregular repetitive pattern can be created using a chair-side rotary instrument on the surface of the shell 10 to resurface the outer surface 14 of the shell 10.

The outer surface 14 of the shell 10 can be then cleaned to ensure removal of all contaminants. For example, the shell 10 can be cleaned by a high-pressure, high-heat steam cleaning and/or autoclave, antimicrobial cleaning solutions may be applied to the surface to detoxify the contaminated surface.

After filling and reshaping of the shell 10 is completed, the shell 10 and the post 40 are removed from the implant 30 by un-screwing the retaining screw 50 at step 240. The shell 10 and the coupled post 40 are then cleaned and inspected and all voids are filled and re-surfaced and cleaned as described above.

At step 242, a healing abutment can be coupled to the implant 30. For example, a standard cylindrical healing abutment composed of titanium, stainless steel, anodized metal or other metal can be utilized. In another example, the cylindrical healing abutment can be made from a polymer and disposed of after removal to save costs. The healing abutment is selected to couple to the implant 30 resulting in a noticeable gap between the outer surface 14 of the healing abutment and the bone socket 102. At step 244, bone grafting materials can be placed within the gap between the bone socket 102 and surface of the implant 30 at or below the crest of bone 110. A barrier membrane can be positioned (if necessary) before or after the bone grafting materials are placed in the gap. At step 246, the healing abutment is removed and the contoured refinished soft-tissue-preservation abutment formed by the luted shell 10 and the post 40 inserted. The soft-tissue-preservation abutment can be retained to the implant 30 by replacing the retaining screw 50 and applying a seating torque to the screw 50 (e.g., between approximately 15 newton-centimeters to approximately 35 newton-centimeters).

Accordingly, the healing abutment can be used as intra-operative component that is placed during the process 200 to allow bone grafting materials to be placed within the gap between the implant 30 and the bone socket 102. The healing abutment also prevents the bone grafting materials from entering into a bore of the implant 30 prior to the replacement of the shell 10 and the post 40. The healing abutment can be a single use, disposable component. It is contemplated that the healing abutment can be fabricated from a variety of materials and come in a variety of heights and widths. It is also contemplated that, according to some aspects, one or more of the healing abutments can be included in the kits described herein.

At step 248, the shell 10 can be adjusted to ensure that it is not in occlusal contact with the opposing teeth 104 when the patient closes their mouth. At step 250, a final radiograph can be taken to assess the fit and position of the implant 30 and shell 10.

As a result of the process 200, the temporary soft-tissue-preservation abutment formed from the shell 10 and the post 40 creates a biologic-seal to the underlying soft tissue and preserves the integrity of the surrounding gingival architecture. According to some aspects, the temporary soft-tissue-preservation abutment may retained in the soft-tissue socket 100 for at least approximately 3-4 months at which time the fabrication of the final prosthesis can be initiated.

Referring now to FIGS. 10A-14B, exemplary shells 310 are illustrated according to alternative aspects of the present invention. Each shell 310 is substantially similar to the shell 10 described and illustrated with respect to FIGS. 1-6, except instead of the shell 10 being mechanically decoupled from the post 40 as in FIGS. 1-6, the shell 310 is adjustably coupled to a post 340 prior to a luting compound 60 being applied. That is, the shell 310 and the post 340 are adjustably coupled prior to placement of the shell 310 in the soft-tissue socket 100 and attachment of the post 340 to the implant 30. It has been found that adjustably coupling the shell 310 and the post 340 in this manner can simplify the placement of the shell 310 and the post 340 in the soft-tissue socket 100 and the coupling of the post 40 to the implant 30.

As described above, it is important to allow the position of the shell 310 to be determined by the soft-tissue socket 100 as opposed to the position of the implant 30, which may be determined by the bone socket 102 in which the implant 30 is placed. Advantageously, the shell 310 can be independently positioned relative to the implant 30 because the shell 310 is adjustably coupled to the post 340 as opposed to fixedly coupled to the post 340 (prior to the luting compound 60 being applied). According to aspects of the present invention, the shell 310 is adjustably coupled to the post 340 by a plurality of spokes 342 that extend from an inner surface 315 of the shell 310 to an outer surface 344 of the post 340. The spokes 342 are configured to allow adjustment of the relative positions of the shell 310 and the post 340.

In the example illustrated in FIGS. 10A-10E, the plurality of spokes 342 are provided as hinged arms that allow the post 340 to be moved and rotated in all directions (i.e., in the x-, y- and z-directions and with freedom of rotation about all three axes). For example, the hinged arms can be configured to bend, expand, and/or compress in the x-, y-, and z-directions. In this way, the range of relative movement and positioning between the shell 310 and the post 340 allows for the shell axis 12 and the implant axis 32 to be unaligned (in a manner similar to that described above for the shell 10 of FIGS. 1-6 and 8) when the post 340 is coupled to the implant 30 and the shell 340 is placed in the soft-tissue socket 100.

The shells 310 illustrated in FIGS. 11A-14B provide additional non-limiting examples of different configurations for the plurality of spokes 342. While the shells 310 are illustrated as having symmetric shapes, it should be understood that the shells 310 can have the shape(s) described above and illustrated with respect to the shell 10 of FIGS. 1-8. In each example, the plurality of spokes 342 provide simultaneous coupling and freedom of movement between the shell 310 and the post 340. In the example illustrated in FIGS. 11A-11B, the shell 310 is adjustably coupled to the post 340 by two spokes 342, each having a single hinge between the inner surface 315 of the shell 310 and the outer surface 344 of the post 340. In the example illustrated in FIGS. 12A-12B, the shell 310 is adjustably coupled to the post 340 by two spokes 342 configured as D-shaped members extending between the inner surface 315 of the shell 310 and the outer surface 344 of the post 340. In the example illustrated in FIGS. 13A-13B, the shell 310 is adjustably coupled to the post 340 by three spokes 342 in a spiral configuration. In the example illustrated in FIGS. 14A-14B, the shell 310 is adjustably coupled to the post 340 by three spring-shaped spokes 342. Accordingly, it should be understood that the plurality of spokes 342 can be provided in a wide variety of configurations that adjustably couple the shell 310 to the post 340 to allow for simultaneous placement of the shell 310 and the post 340 in the soft-tissue socket 100 while still allowing the shell 310 to be independently positioned relative to the post 340 when coupled to the implant 30.

It should be understood that the shell 310 adjustably coupled to the post 340 can be employed utilizing the process 200 described above and illustrated in FIG. 9. Because the shell 310 is adjustably coupled to the post 340, the shell 310 and the post 340 are placed in the soft-tissue socket 100 simultaneously. According to some aspects, the shell 310 can be fully placed in the soft-tissue socket 100 at the same time as the post 340 is coupled to the implant 30. According to other aspects, the shell 310 can be fully positioned in the soft-tissue socket 100 prior to the post 340 being coupled to the implant 30. According to still other aspects, the post 340 can be coupled to the implant 30 prior to the shell 310 being fully placed in the soft-tissue socket 100.

According to some aspects of the present disclosure, the shell 310 can be made from the same materials described above with respect to the shell 10 of FIGS. 1-9. That is, the shell 310 can be made from a material having a color that is configured to substantially match or mimic patient specific conditions or the shell 310 can be made from a material having transparency (for use with a luting compound 60 having a color that is configured to substantially match or mimic patient specific conditions). According to other aspects of the present disclosure, the shell 310 can be made of any biocompatible material(s) regardless of color or transparency such as, for example, ceramic (e.g., zirconium oxide ceramic), acrylic, porcelain, lithium disilicate, zirconia and other crystalline structure. Additionally, it is contemplated that the material of the shell 310 can include anti-microbial, bacteriostatic properties to retard the growth or colonization of the surface and internal surfaces with micro-organisms. Non-limiting examples of such materials can include silver, copper, magnesium, titanium, hydroxyapitite, etc. These anti-microbial, bacteriostatic materials can be incorporated into the shell material or may be applied to the shell surface forming a second layer.

Figure 7:
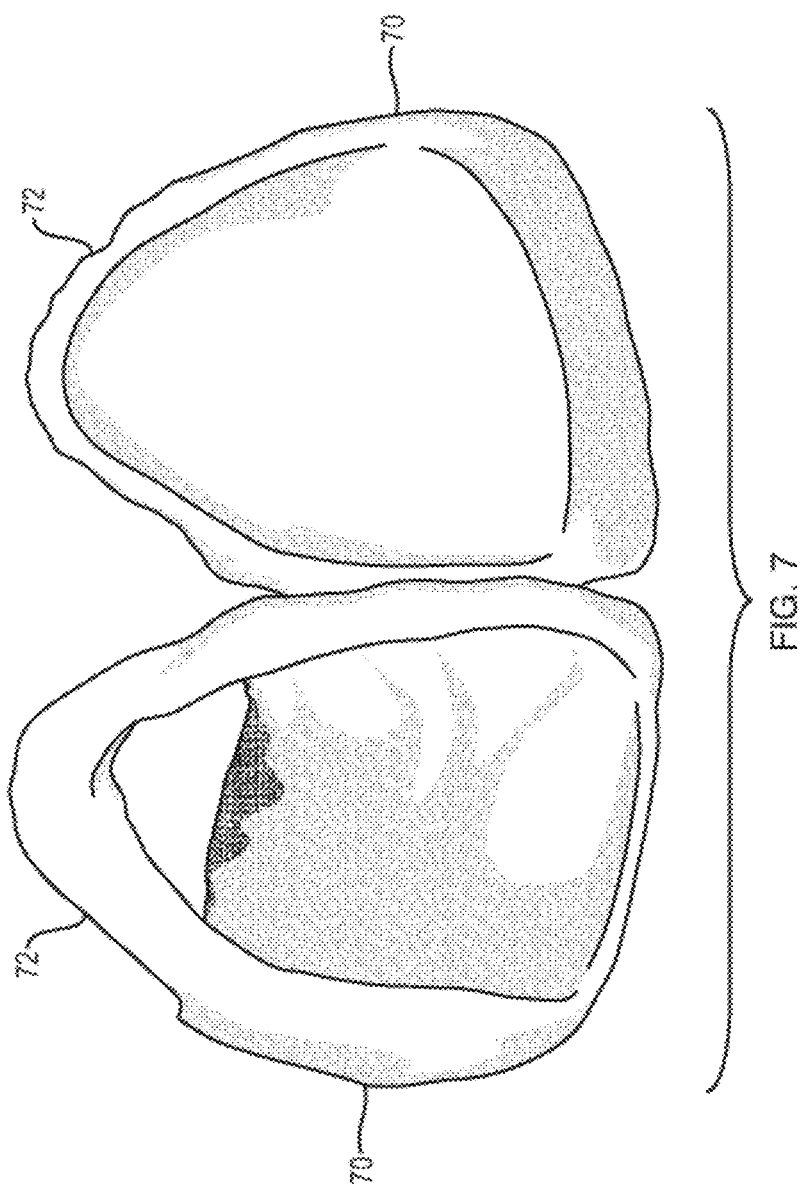
FIG. 7 is a composite, side-by-side, rear (lingual) and front (facial) perspective view of an immediate tooth-form temporary according to aspects of the present invention.

In the examples illustrated and described above for FIGS. 1-6, 8, and 10A-14B, the shells 10, 310 generally extend from the crest of the bone 110 to approximately the height of the remaining soft tissue 108. However, according to according to additional and/or alternative aspects of the present disclosure, the shell 10, 310 can also be modified to provide a tooth form temporary 70. An example tooth-form temporary (provisional) 70 is shown in FIG. 7. The tooth-form temporary includes a subgingival transmucosal section 72 that is based on the shell 10, 310 and a supragingival section shaped like a tooth. The tooth-form temporary 70 extends from the implant-platform of the luted shell 10, 310, and extends from the outer perimeter 18 of shell 10, 310 beyond the level of the free-gingival margin to the incisal edge or occlusal surface of the dental tooth it is replacing.

The tooth-form temporary 70 can be provided in a plurality of different vertical heights, elliptical shapes and different dimensions to temporally replace the various types of teeth that might be extracted. It is contemplated that the plurality of tooth-form temporaries 70 can be provided as a kit in which a variety of different sizes, shapes and types are available to replace different teeth that are extracted. As non-limiting examples, the tooth-form temporary 70 can be made of a material such as polymethyl methacrylate (PMMA), polyetheretherketone (PEEK), lithium disilicate, or zirconium dioxide.

As described above, the shells 10, 310 and the temporary soft-tissue-preservation abutments formed therefrom of the present disclosure can achieve a number of advantageous functionalities with improved esthetics. In particular, the shells 10, 310 and the temporary soft-tissue-preservation abutments preserve the soft tissue architecture after the immediate removal of a tooth, reestablish a biologic seal with the soft-tissue socket 100, support the soft tissues to prevent collapse of bone and soft tissue during healing, promote soft tissue adhesion by providing direct physical contact between the temporary soft-tissue-preservation abutment and the surrounding soft-tissue socket 100, and/or retain bone regeneration materials in a gap between the implant 30 and the bone socket 102. According to some aspects, the process of forming the temporary soft-tissue-preservation abutment can be simplified without sacrificing the above-functionalities by precoupling the shell 310 and the post 340 in an adjustable manner. According to further aspects, improved esthetics can be achieved forming the shells 10, 310 form a material having a color configured to mimic the patient-specific conditions at an implantation site or forming the shells 10, 310 from a material having transparency such that a luting compound 60 having a color configured to mimic the patient-specific conditions may be visible.

The emergence profile of the shell 10, 310 can have a variety of profiles to compensate for the position of the implant 30 within the bone socket 102. Since the implant 30 may be intentionally placed off-center from the extracted tooth, the shell 10, 310 can be intentionally placed eccentric to the implant 30 placed within the bone 102. That is, the shell 10, 310 can be placed eccentric to the implant 30. The emergence profile of the shell 10, 310 can be over-compensated and/or under-compensated in the profile design allowing for the position of the implant 30. The compensating emergence profile design and ability to place the shell 10, 310 eccentric enables the re-establishment of an effective biologic-seal between the outer surface 14 of the shell 10 and the soft-tissue socket 100. That is, the subgingival shape of the soft-tissue-preservation abutment promotes biological socket seal by providing either an over-contoured or an under-contoured emergence profile to compensate for the position of the dental implant 30 (e.g., in the vertical, horizontal, and buccal-lingual, mesial-distal angulations) and provide an adequate soft tissue seal between prosthesis and soft-tissue socket 100 to support the soft tissues to preserve the natural architecture of the gingival tissues.

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

What is claimed is:

1. A soft tissue preservation arrangement comprising:
   a hollow shell defining an interior volume extending from a proximal opening to a distal opening, the proximal opening being defined by a first perimeter that is smaller than a second perimeter defining the distal opening such that the shell tapers outwardly from the first perimeter to the second perimeter, the second perimeter having an asymmetrically scalloped shape including a distal peak, a mesial peak opposite the distal peak, a lingual valley between the distal peak and the mesial peak, and a facial valley between the distal peak and the mesial peak, wherein the hollow shell is transparent.

2. The arrangement of claim 1, wherein the hollow shell is semi-transparent.

3. The arrangement of claim 1, further comprising a luting compound for coupling the hollow shell to a post positioned in the interior volume, the luting compound having a color configured to correspond to a color of a gingival tissue at an implantation site, the luting compound being visible through a surface of the shell.

4. The arrangement of claim 3, wherein the luting compound is a pink color.

5. The arrangement of claim 3, wherein the luting compound is a brown color or a blue color.

6. The arrangement of claim 1, further comprising a luting compound for coupling the hollow shell to a post positioned in the interior volume, the luting compound having a color configured to correspond to a color of a tooth adjacent to an implantation site, the luting compound being visible through a surface of the shell.

7. The arrangement of claim 1, wherein the shell has a pink color.

8. The arrangement of claim 1, further comprising:
   a post configured to be coupled to an implant; and
   a plurality of spokes adjustably coupling an outer surface of the post to an inner surface of the shell, the plurality of spokes being configured to allow the shell to be adjustably moved relative to the post.

9. The arrangement of claim 1, wherein the shell is mechanically decoupled from a post prior to a luting compound being applied to the shell and the post.

10. A soft tissue preservation arrangement comprising:
    a hollow shell defining an interior volume extending from a proximal opening to a distal opening, the proximal opening being defined by a first perimeter that is smaller than a second perimeter defining the distal opening such that the shell tapers outwardly from the first perimeter to the second perimeter, the second perimeter being asymmetrically scalloped;
    a post configured to be coupled to a dental implant; and
    a plurality of spokes adjustably coupling the post to the hollow shell, the plurality of spokes being configured to allow the shell to be adjustably moved relative to the post.

11. The arrangement of claim 10, wherein the plurality of spokes are configured to allow the shell to be moved in an x-dimension, a y-dimension, and a z-dimension.

12. The arrangement of claim 11, wherein the plurality of spokes are further configured to allow the shell to be rotated about the x-dimension, the y-dimension, and the z-dimension.

* * * * *